(12) United States Patent
Held et al.

(10) Patent No.: US 9,018,451 B2
(45) Date of Patent: Apr. 28, 2015

(54) OPTIMIZED EXPRESSION OF GLYPHOSATE RESISTANCE ENCODING NUCLEIC ACID MOLECULES IN PLANT CELLS

(75) Inventors: Bruce Held, Ames, IA (US); Vaithilingam Sekar, Ames, IA (US); Terry Wright, Westfield, IN (US); Sean Russell, Indianapolis, IN (US)

(73) Assignee: M S Technologies, LLC, West Point, IA (US)

( * ) Notice: Subject to any disclaimer, the term of this patent is extended or adjusted under 35 U.S.C. 154(b) by 572 days.

(21) Appl. No.: 13/303,502

(22) Filed: Nov. 23, 2011

(65) Prior Publication Data

US 2012/0144530 A1 Jun. 7, 2012

Related U.S. Application Data

(60) Provisional application No. 61/419,703, filed on Dec. 3, 2010.

(51) Int. Cl.
  *C12N 15/82* (2006.01)
  *C12N 9/10* (2006.01)
(52) U.S. Cl.
  CPC .......... *C12N 9/1092* (2013.01); *C12N 15/8275* (2013.01)
(58) Field of Classification Search
  CPC .............................. C12N 9/1022; C12N 9/1092
  See application file for complete search history.

(56) References Cited

U.S. PATENT DOCUMENTS

| | | | |
|---|---|---|---|
| 4,535,060 A | 8/1985 | Comai | |
| 4,769,061 A | 9/1988 | Comai | |
| 4,940,835 A | 7/1990 | Shah et al. | |
| 5,094,945 A | 3/1992 | Comai | |
| 5,310,667 A | 5/1994 | Eichholtz | |
| 5,380,831 A | 1/1995 | Adang | |
| 5,436,391 A | 7/1995 | Fujimoto | |
| 5,491,288 A | 2/1996 | Chaubet | |
| 5,510,471 A | 4/1996 | Lebrun | |
| 5,633,435 A * | 5/1997 | Barry et al. ................... | 800/288 |
| 5,633,448 A | 5/1997 | Lebrun | |
| 5,866,775 A | 2/1999 | Eichholtz | |
| RE36,449 E | 12/1999 | Lebrun | |
| 6,040,497 A | 3/2000 | Spencer | |
| 6,225,114 B1 | 5/2001 | Eichholtz et al. | |
| 6,248,876 B1 | 6/2001 | Barry | |
| 6,566,587 B1 * | 5/2003 | Lebrun et al. ................ | 800/300 |
| 6,673,990 B2 | 1/2004 | Cardineau et al. | |
| 7,045,684 B1 | 5/2006 | Held et al. | |
| 7,105,332 B2 | 9/2006 | Abad et al. | |
| 7,250,561 B1 * | 7/2007 | Pallett et al. ................. | 800/300 |
| 7,626,077 B2 | 12/2009 | Held | |
| 7,700,103 B2 | 4/2010 | Bryan | |
| 7,807,791 B2 | 10/2010 | Held et al. | |
| RE41,943 E | 11/2010 | Held | |
| 2007/0295251 A1 | 12/2007 | Heinrichs | |
| 2009/0082299 A1 | 3/2009 | Felber | |
| 2013/0055453 A1 | 2/2013 | Hoffman | |

FOREIGN PATENT DOCUMENTS

| | | |
|---|---|---|
| EP | 1217073 B1 | 3/2006 |
| WO | WO9704103 A2 | 2/1997 |
| WO | WO0066748 A1 | 11/2000 |
| WO | WO2008141154 A2 | 11/2008 |
| WO | WO2012074868 A2 | 6/2012 |
| WO | WO2012075426 A1 | 6/2012 |
| WO | WO2012075429 A1 | 6/2012 |
| WO | WO2012075426 A1 | 7/2012 |
| WO | WO2012075429 A1 | 7/2012 |
| WO | WO2013010094 A1 | 1/2013 |

OTHER PUBLICATIONS

Kawabe et al 2003 Genes Genet. Syst. 78: 343-352.*
Green et al 2008 Pest Management Science 64: 332-339.*
Cui et al., U.S. Appl. No. 13/991,246, Stacked herbicide tolerance event 8264.44.06.1, related transgenic soybean lines, and detection thereof, filed Jun. 3, 2013.
Cui et al., U.S. Appl. No. 13/991,309, Stacked herbicide tolerance event 8291.45.36.2, related transgenic soybean lines, and detection thereof, filed Jun. 3, 2013.
Geneseq Accession No. AAH49585 "Partial sequence #8 of recombinent gene in genetically modified maize" Sep. 24, 2001, XP002687140.
GenBank Accession No. AX463795 "Sequence 4 from Patent EP1217073" Jul. 15, 2007, XP002687141.
GenBank Accession No. X63374 "*Z. mays* mRNA for EPSPS-synthase" Sep. 4, 1996, XP002687142.
Streatfield et al. "Approaches to achieve high-level heterologous protein production in plants" Plant Biotechnology Journal (2007)5:pp. 2-15.
Campbell et al. "Codon Usage in higher plants, green algae and cyanobacteria" Plant Physiol. (1990)92,1-11.
Geyer et al. "Translational control of recombinant human acetylcholinesterase accumulation in plants" BMC Biotechnology, B2007,7:27, doi:10.1 186/1472-6750-7-27.
EPO written opinion, PCT/US2011/062014 Nov. 23, 2012.
Klee et al. 1987 Cloning of an *Arabidopsis thaliana* gene encoding 5-enolpyruvyl-shikimic acid-3-phosphate synthase: sequence analysis and manipulation to obtain glyphosate-tolerant plants. Mol. Gen. Genet. 210: 437-442.
Green 2009 "Evolution of glyphosate-resistant crop technology" Weed Science 57:108-117.
Ruff et al. "Effects of amino acid substitutions on glyphosate tolerance and activity of EPSPS Synthase" Plant Physiology, vol. 96 (Supp. 1) p. 94, 1991. mpbell et al. "Codon usage in higher plants, green algae and cyanobaceria" Plant Physiol. 92 1-11 (1990).
Murray et al. "Codon usage in plant genes" Nucleic Acids Res. 17:4777-4998 (1989).
Ca
Kozak "Point mutations define a sequence flanking the AUG initiator codon that modulates translation by eukaryotic ribosomes" Cell 44(2):283-92 (1986).
Kozak "An analysis of 5' encoding sequences from 699 vertebrate messenger RNAs" Nucl. Acids Res. 15(20):8125-8148 (1987).
Funke et al. "Structural Basis of Glyphosate Resistance Resulting from the Double Mutation Thr973Ile and Pro1013Ser in 5-Enolpyruvylshikimate-3-phosphate Synthase from *Escherichia coli*" Journal of Biological Chemistry vol. 284, No. 15, pp. 9854-9860 (2009).

* cited by examiner

*Primary Examiner* — David H Kruse
(74) *Attorney, Agent, or Firm* — Patricia A. Sweeney

(57) ABSTRACT

A nucleic acid molecule encoding a 5-enolpyruvyl-3-phosphoshikimic acid synthase (EPSPS) that provides resistance to glyphosate is provided, that has been optimized for expression in both monocotyledonous and dicotyledonous plants and preferably in soybeans. Methods of use are also provided.

22 Claims, 8 Drawing Sheets

Figure 1

GenBank Accession #: X63374 line 1; amino acid line 2

(atg)

```
gcggtgccgaggagatcgtgctgcagccatcaaggagatc
 A  G  E  E  I  V  L  Q  P  I  K  E  I
tccgcacgtcaagctgccgggtccagtcgtttccaaccgg
 S  G  T  V  K  L  P  G  S  K  S  L  S  N  R
atcctcctgcagcgctgtccgaggggacaacagtggttgat
 I  L  L  A  A  L  S  G  T  V  V  D
aacttgctgaacagtgaggatgtcactacatgctgggactt
 N  L  L  N  S  E  D  V  T  Y  M  L  G  A  L
aggactcttggtctctctgtcgaagcggacaaagctgccaaaga
 R  T  L  S  L  S  V  E  A  D  K  A  A  K  R
gctgtagtgtgggctgtggtggaaagtccccagttgaggatgct
 A  V  V  V  G  C  G  G  K  F  P  V  E  D  A
aaagaggaagtgcagctctcttgggaatgctggaactgcaatg
 K  E  E  V  Q  L  F  L  G  N  A  G  T  A  N (T122A)
cggcattgacagcagctgttactgctgctggtggaaatgcaact
 R  P (T165I) T  A  A  V  T  A  A  G  G  N  T
tactgcttgatggagtacaagaatgaggagagaccattgga
 T  Y  C  V  L  D  G  V  P  M  R  E  R  P  I  G
gactggttgtcggattgaagcagctggtgcagatgttgattgt
 D  L  V  V  G  L  K  Q  L  G  A  D  V  D  C
ttccttggaactgactgccacacttgttgtgtcaatggaatgga
 F  L  G  T  D  C  P  P  V  R  V  N  G  I  G
gggctacctggtggcaaggtcaagctgtctggtcatcagcagt
 G  L  P  G  G  K  V  K  L  S  G  S  I  S  S
cagttacttgagtgccttgctgatggctgtccttctggtcttggg
 Q  Y  L  S  A  L  L  M  A  A  P  L  A  L  G
gatgtggagattgaaatcattgataaatcaatctccattcgtac
 D  V  E  I  E  I  I  D  K  L  I  S  I  P  Y
gtcgaaatgacattgagattgatggagcgtttggtgtgaaagca
 V  E  M  T  L  R  L  M  E  R  F  G  V  K  A
gagcatctgatagctgggacagatctacatcaaggaggtcaa
 E  H  S  D  S  G  T  D  L  H  K  G  G  Q
aaatacaagtcccctaaaatgctatgtgaggtgatgctcca
 K  Y  K  S  P  K  N  A  Y  V  E  G  D  A  S
agcgcaagctattcctaggctggtgctgcaattactggaaggact
 S  A  S  Y  F  L  A  G  A  A  I  T  G  G
gtgactgtggaaggttgtggcaccaccagtttgcaggtgatgtg
 V  T  V  E  G  C  G  T  T  S  L  Q  G  D  V
aagtttgctgaggtactggagatgatgggagcgaaggttacatgg
 K  F  A  E  V  L  E  M  M  G  A  K  V  T  W
accgagactagctaactgttactggccaccgcgggagccattt
 T  E  T  S  V  T  V  T  G  P  P  R  E  P  F
gggaggaaacatcctcaaggcgattgatgtcaacatgaacaagatg
 G  R  K  H  L  K  A  I  D  V  N  M  N  K  M
cctgatgtagccatgactctgctgtggtgcctcttgcagat
 P  D  V  A  N  T  L  A  V  V  A  L  F  A  D
ggcccgacacgcatcagagaggtggcttcctggagagtaaggag
 G  P  T  R  I  R  D  V  A  S  W  R  V  K
accgagaggatggttcgatcggacggagctaaccagctgga
 T  E  R  S  V  A  I  R  T  E  L  T  K  L
gcatctgtcgaggaagggccggatactgatcatacgcaggcg
 A  S  V  E  E  G  P  D  Y  C  I  T  P  P
gagaagctgaacgtgacgggcatcgacacgtacgacgaccacagg
 E  K  L  N  V  T  A  I  D  T  Y  D  D  H
atggctatgccttctctcgcagcgtgaggtccgtc
 M  A  M  A  F  S  L  A  A  C  A  E  V  P  V
accatcaggaccctggtgcaacggagacttccccgactac
 T  I  R  D  P  G  C  T  R  K  T  F  P  D  Y
tcgatgtgctggagacttgtaagaattaa
 F  D  V  L  E  T  F  V  K *
```

Figure 2

*Z. mays* encoding 2mEPSPS

*atg*gccggcgccgaggagatcgtgctgcagcccatcaaggagatctccggcaccgtcaagctgccggggtccaagtcgcttt
ccaaccggatcctcctactcgccgccctgtccgaggggacaacagtggttgataacctgctgaacagtgaggatgtccactaca
tgctcggggccttgaggactcttggtctctctgtcgaagcggacaaagctgccaaaagagctgtagttgttggctgtggtggaa
gttcccagttgaggatgctaaagaggaagtgcagctcttcttggggaatgctggaatcgcaatgcggtccttgacagcagctgtt
actgctgctggtggaaatgcaacttacgtgcttgatggagtaccaagaatgagggagagacccattggcgacttggttgtcggat
tgaagcagcttggtgcagatgttgattgtttccttggcactgactgcccacctgttcgtgtcaatggaatcggagggctacctggtg
gcaaggtcaagctgtctggctccatcagcagtcagtacttgagtgccttgctgatggctgctcctttggctcttggggatgtggag
attgaaatcattgataaattaatctccattccgtacgtcgaaatgacattgagattgatggagcgttttggtgtgaaagcagagcattc
tgatagctgggacagattctacattaagggaggtcaaaaatacaagtcccctaaaaatgcctatgttgaaggtgatgcctcaagc
gcaagctatttcttggctggtgctgcaattactggagggactgtgactgtggaaggttgtggcaccaccagtttgcagggtgatgt
gaagtttgctgaggtactggagatgatgggagcgaaggttacatggaccgagactagcgtaactgttactggcccaccgcggg
agccatttgggaggaaacacctcaaggcgattgatgtcaacatgaacaagatgcctgatgtcgccatgactcttgctgtggttgcc
ctctttgccgatggcccgacagccatcagagacgtggcttcctggagagtaaaggagaccgagaggatggttgcgatccggac
ggagctaaccaagctgggagcatctgttgaggaagggccggactactgcatcatcacgccgccggagaagctgaacgtgacg
gcgatcgacacgtacgacgaccacaggatggcgatggctttctccctgccgcctgtgccgaggtccccgtcaccatccggga
ccctgggtgcacccggaagaccttccccgactacttcgatgtgctgagcactttcgtcaagaattaa

Figure 3

DMMG optimized encoding 2mEPSPS (atg)
    gctggagctgaagagattgtgctccaacccatcaaggagatctctggcacagtcaaactccctggctcaaagtcacttc
aaaccgtatcctcttgcttgcagctcttctgaagggaccacagtggttgacaaccttctcaactcagaggatgtccactacatgct
cggagccttgaggactcttggcttgtctgttgaagcagacaaagctgccaagcgtgctgtgtggttggctgtggtggaaagtcc
cagttgaagatgccaaaggaagtccagctcttccttgggaatgctgggattgccatgagatccttgactgcagctgtcactgc
agctggtgggaatgccacctatgttcttgatggcgtgccacgcatgagggagagaccattggcgacttggtggttggcttgaag
caactggagctgatgttgactgcttccttggcaccgactgtccacctgtcgtgtcaatgggattggaggtctccctggtggcaag
gtcaagctctctggctccatcagctcccagtacttgtcagccttgctcatggcagctccctggctcttggtgatgtggagattgag
atcattgacaaactcatctccattccctatgtggagatgaccttgagattgatggaaaggttggtgtgaaagctgagcattctgaca
gctgggacagattctacatcaagggaggtcagaagtacaagtcacccaagaatgcctatgttgaaggtgatgccagctctgcca
gctacttcttggctggtgctgcaatcactggaggactgtgacagtggaaggttgtggcactaccagcttgcaaggtgatgtgaa
gtttgctgaggtgcttgagatgatgggagcaaaggtcacctggactgaaacctccgtcacagtgactggacctccaagggagcc
attcggaaggaaacatctcaaagccattgatgtcaacatgaacaagatgccagatgttgccatgactcttgctgtggttgcactctt
gccgatggaccaacagccatcagagatgtggcttcctggagagtcaaggagacagagaggatggttgcaatacgcacagagt
tgaccaaacttggagccagcgttgaggaaggaccagactactgcatcatcacacctcccgagaagctcaacgtgacagccata
gacacctatgatgaccacgcatggcaatggctttctccttgcagcctgtgcagaagtccctgtcaccatacgtgaccctgggt
gcactcgcaagacctcccagactacttgatgtgctcagcacctttgtcaagaactga

Lanes 1 and 18: Molecular markers
Lanes 2-5: 2mEPSPS protein standard at 2, 1, 0.5 and 0.25 ng/well
Lanes 6-9: Unsprayed soybean events with optimized 2mEPSPS
Lanes 10-13: Sprayed* soybean events with optimized 2mEPSPS
Lanes 14-16: Unsprayed soybean events with un-optimized 2mEPSPS
Lane 17: Non-transgenic variety 'Maverick'

Lanes 1 and 18: Molecular markers
Lanes 2-5: 2mEPSPS protein standard at 2, 1, 0.5 and 0.25 ng/well
Lanes 6-9: Unsprayed soybean events with optimized 2mEPSPS
Lanes 10-13: Sprayed* soybean events with optimized 2mEPSPS
Lanes 14-16: Unsprayed soybean events with un-optimized 2mEPSPS
Lane 17: Non-transgenic variety 'Maverick'

SEQUENCE LISTING

```
<160> NUMBER OF SEQ ID NOS: 7

<210> SEQ ID NO 1
<211> LENGTH: 1335
<212> TYPE: DNA
<213> ORGANISM: Zea mays
<220> FEATURE:
<221> NAME/KEY: CDS
<222> LOCATION: (1)..(1332)

<400> SEQUENCE: 1 gcg ggt gcc gag gag atc gtg ctg cag ccc atc aag gag atc tcc ggc      48
Ala Gly Ala Glu Glu Ile Val Leu Gln Pro Ile Lys Glu Ile Ser Gly
1               5                   10                  15 acc gtc aag ctg ccg ggg tcc aag tcg ctt tcc aac cgg atc ctc cta      96
Thr Val Lys Leu Pro Gly Ser Lys Ser Leu Ser Asn Arg Ile Leu Leu
            20                  25                  30 ctc gcc gcc ctg tcc gag ggg aca aca gtg gtt gat aac ctg ctg aac     144
```

|  |  |  |  |  |  |  |  |  |  |  |  |  |  |  |
|---|---|---|---|---|---|---|---|---|---|---|---|---|---|---|
| Leu | Ala | Ala | Leu | Ser | Glu | Gly | Thr | Thr | Val | Val | Asp | Asn | Leu | Leu | Asn |
| | | 35 | | | | 40 | | | | 45 | | | | |

```
agt gag gat gtc cac tac atg ctc ggg gcc ttg agg act ctt ggt ctc      192
Ser Glu Asp Val His Tyr Met Leu Gly Ala Leu Arg Thr Leu Gly Leu
 50                  55                  60 tct gtc gaa gcg gac aaa gct gcc aaa aga gct gta gtt gtt ggc tgt      240
Ser Val Glu Ala Asp Lys Ala Ala Lys Arg Ala Val Val Val Gly Cys
65                   70                  75                  80 ggt gga aag ttc cca gtt gag gat gct aaa gag gaa gtg cag ctc ttc      288
Gly Gly Lys Phe Pro Val Glu Asp Ala Lys Glu Glu Val Gln Leu Phe
                 85                  90                  95 ttg ggg aat gct gga act gca atg cgg cca ttg aca gca gct gtt act      336
Leu Gly Asn Ala Gly Thr Ala Met Arg Pro Leu Thr Ala Ala Val Thr
             100                 105                 110 gct gct ggt gga aat gca act tac gtg ctt gat gga gta cca aga atg      384
Ala Ala Gly Gly Asn Ala Thr Tyr Val Leu Asp Gly Val Pro Arg Met
         115                 120                 125 agg gag aga ccc att ggc gac ttg gtt gtc gga ttg aag cag ctt ggt      432
Arg Glu Arg Pro Ile Gly Asp Leu Val Val Gly Leu Lys Gln Leu Gly
     130                 135                 140 gca gat gtt gat tgt ttc ctt ggc act gac tgc cca cct gtt cgt gtc      480
Ala Asp Val Asp Cys Phe Leu Gly Thr Asp Cys Pro Pro Val Arg Val
145                 150                 155                 160 aat gga atc gga ggg cta cct ggt ggc aag gtc aag ctg tct ggc tcc      528
Asn Gly Ile Gly Gly Leu Pro Gly Gly Lys Val Lys Leu Ser Gly Ser
                 165                 170                 175 atc agc agt cag tac ttg agt gcc ttg ctg atg gct gct cct ttg gct      576
Ile Ser Ser Gln Tyr Leu Ser Ala Leu Leu Met Ala Ala Pro Leu Ala
             180                 185                 190 ctt ggg gat gtg gag att gaa atc att gat aaa tta atc tcc att ccg      624
Leu Gly Asp Val Glu Ile Glu Ile Ile Asp Lys Leu Ile Ser Ile Pro
         195                 200                 205 tac gtc gaa atg aca ttg aga ttg atg gag cgt ttt ggt gtg aaa gca      672
Tyr Val Glu Met Thr Leu Arg Leu Met Glu Arg Phe Gly Val Lys Ala
     210                 215                 220 gag cat tct gat agc tgg gac aga ttc tac att aag gga ggt caa aaa      720
Glu His Ser Asp Ser Trp Asp Arg Phe Tyr Ile Lys Gly Gly Gln Lys
225                 230                 235                 240 tac aag tcc cct aaa aat gcc tat gtt gaa ggt gat gcc tca agc gca      768
Tyr Lys Ser Pro Lys Asn Ala Tyr Val Glu Gly Asp Ala Ser Ser Ala
                 245                 250                 255 agc tat ttc ttg gct ggt gct gca att act gga ggg act gtg act gtg      816
Ser Tyr Phe Leu Ala Gly Ala Ala Ile Thr Gly Gly Thr Val Thr Val
             260                 265                 270 gaa ggt tgt ggc acc acc agt ttg cag ggt gat gtg aag ttt gct gag      864
Glu Gly Cys Gly Thr Thr Ser Leu Gln Gly Asp Val Lys Phe Ala Glu
         275                 280                 285 gta ctg gag atg atg gga gcg aag gtt aca tgg acc gag act agc gta      912
Val Leu Glu Met Met Gly Ala Lys Val Thr Trp Thr Glu Thr Ser Val
     290                 295                 300 act gtt act ggc cca ccg cgg gag cca ttt ggg agg aaa cac ctc aag      960
Thr Val Thr Gly Pro Pro Arg Glu Pro Phe Gly Arg Lys His Leu Lys
305                 310                 315                 320 gcg att gat gtc aac atg aac aag atg cct gat gtc gcc atg act ctt     1008
Ala Ile Asp Val Asn Met Asn Lys Met Pro Asp Val Ala Met Thr Leu
                 325                 330                 335 gct gtg gtt gcc ctc ttt gcc gat ggc ccg aca gcc atc aga gac gtg     1056
Ala Val Val Ala Leu Phe Ala Asp Gly Pro Thr Ala Ile Arg Asp Val
             340                 345                 350
```

```
gct tcc tgg aga gta aag gag acc gag agg atg gtt gcg atc cgg acg    1104
Ala Ser Trp Arg Val Lys Glu Thr Glu Arg Met Val Ala Ile Arg Thr
        355                 360                 365 gag cta acc aag ctg gga gca tct gtt gag gaa ggg ccg gac tac tgc    1152
Glu Leu Thr Lys Leu Gly Ala Ser Val Glu Glu Gly Pro Asp Tyr Cys
    370                 375                 380 atc atc acg ccg ccg gag aag ctg aac gtg acg gcg atc gac acg tac    1200
Ile Ile Thr Pro Pro Glu Lys Leu Asn Val Thr Ala Ile Asp Thr Tyr
385                 390                 395                 400 gac gac cac agg atg gcc atg gcc ttc tcc ctt gcc gcc tgt gcc gag    1248
Asp Asp His Arg Met Ala Met Ala Phe Ser Leu Ala Ala Cys Ala Glu
                405                 410                 415 gtc ccc gtc acc atc cgg gac cct ggg tgc acc cgg aag acc ttc ccc    1296
Val Pro Val Thr Ile Arg Asp Pro Gly Cys Thr Arg Lys Thr Phe Pro
            420                 425                 430 gac tac ttc gat gtg ctg agc act ttc gtc aag aat taa                1335
Asp Tyr Phe Asp Val Leu Ser Thr Phe Val Lys Asn
        435                 440
```

<210> SEQ ID NO 2
<211> LENGTH: 444
<212> TYPE: PRT
<213> ORGANISM: Zea mays

<400> SEQUENCE: 2

```
Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255
```

```
Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 3
<211> LENGTH: 444
<212> TYPE: PRT
<213> ORGANISM: Zea mays

<400> SEQUENCE: 3

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Ile Ala Met Arg Ser Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
```

```
            180             185             190
Leu Gly Asp Val Glu Ile Glu Ile Asp Lys Leu Ile Ser Ile Pro
        195             200             205

Tyr Val Glu Met Thr Leu Arg Leu Met Glu Arg Phe Gly Val Lys Ala
    210             215             220

Glu His Ser Asp Ser Trp Asp Arg Phe Tyr Ile Lys Gly Gly Gln Lys
225             230             235             240

Tyr Lys Ser Pro Lys Asn Ala Tyr Val Glu Gly Asp Ala Ser Ser Ala
            245             250             255

Ser Tyr Phe Leu Ala Gly Ala Ala Ile Thr Gly Gly Thr Val Thr Val
                260             265             270

Glu Gly Cys Gly Thr Thr Ser Leu Gln Gly Asp Val Lys Phe Ala Glu
            275             280             285

Val Leu Glu Met Met Gly Ala Lys Val Thr Trp Thr Glu Thr Ser Val
    290             295             300

Thr Val Thr Gly Pro Pro Arg Glu Pro Phe Gly Arg Lys His Leu Lys
305             310             315             320

Ala Ile Asp Val Asn Met Asn Lys Met Pro Asp Val Ala Met Thr Leu
            325             330             335

Ala Val Val Ala Leu Phe Ala Asp Gly Pro Thr Ala Ile Arg Asp Val
                340             345             350

Ala Ser Trp Arg Val Lys Glu Thr Glu Arg Met Val Ala Ile Arg Thr
            355             360             365

Glu Leu Thr Lys Leu Gly Ala Ser Val Glu Glu Gly Pro Asp Tyr Cys
    370             375             380

Ile Ile Thr Pro Pro Glu Lys Leu Asn Val Thr Ala Ile Asp Thr Tyr
385             390             395             400

Asp Asp His Arg Met Ala Met Ala Phe Ser Leu Ala Ala Cys Ala Glu
            405             410             415

Val Pro Val Thr Ile Arg Asp Pro Gly Cys Thr Arg Lys Thr Phe Pro
                420             425             430

Asp Tyr Phe Asp Val Leu Ser Thr Phe Val Lys Asn
        435             440

<210> SEQ ID NO 4
<211> LENGTH: 1338
<212> TYPE: DNA
<213> ORGANISM: Zea mays

<400> SEQUENCE: 4
atggccggcg ccgaggagat cgtgctgcag cccatcaagg agatctccgg caccgtcaag      60
ctgccggggt ccaagtcgct ttccaaccgg atcctcctac tcgccgccct gtccgagggg     120
acaacagtgg ttgataacct gctgaacagt gaggatgtcc actacatgct cggggccttg     180
aggactcttg tctctctgt cgaagcggac aaagctgcca aaagagctgt agttgttggc     240
tgtggtggaa agttcccagt gaggatgct aaagaggaag tgcagctctt cttggggaat     300
gctggaatcg caatgcggtc cttgacagca gctgttactg ctgctggtgg aaatgcaact     360
tacgtgcttg atggagtacc aagaatgagg gagagaccca ttggcgactt ggttgtcgga     420
ttgaagcagc ttggtgcaga tgttgattgt tccttggca ctgactgccc acctgttcgt     480
gtcaatggaa tcggagggct acctggtggc aaggtcaagc tgtctggctc catcagcagt     540
cagtacttga gtgccttgct gatggctgct ccttttggctc ttggggatgt ggagattgaa     600
atcattgata aattaatctc cattccgtac gtcgaaatga cattgagatt gatggagcgt     660
```

```
tttggtgtga aagcagagca ttctgatagc tgggacagat tctacattaa gggaggtcaa      720
aaatacaagt cccctaaaaa tgcctatgtt gaaggtgatg cctcaagcgc aagctatttc      780
ttggctggtg ctgcaattac tggagggact gtgactgtgg aaggttgtgg caccaccagt      840
ttgcagggtg atgtgaagtt tgctgaggta ctggagatga tgggagcgaa ggttacatgg      900
accgagacta gcgtaactgt tactggccca ccgcgggagc catttgggag gaaacacctc      960
aaggcgattg atgtcaacat gaacaagatg cctgatgtcg ccatgactct tgctgtggtt     1020
gccctctttg ccgatggccc gacagccatc agagacgtgg cttcctggag agtaaaggag     1080
accgagagga tggttgcgat ccggacggag ctaaccaagc tggagcatc tgttgaggaa      1140 gggccggact actgcatcat cacgccgccg gagaagctga acgtgacggc gatcgacacg     1200
tacgacgacc acaggatggc gatggctttc tcccttgccg cctgtgccga ggtccccgtc     1260
accatccggg accctgggtg cacccggaag accttccccg actacttcga tgtgctgagc     1320
actttcgtca agaattaa                                                   1338

<210> SEQ ID NO 5
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gctggagctg aagagattgt gctccaaccc atcaaggaga tctctggcac agtcaaactc       60
cctggctcaa agtcactttc aaaccgtatc ctcttgcttg cagctctttc tgaagggacc     120
acagtggttg acaaccttct caactcagag gatgtccact acatgctcgg agccttgagg     180
actcttggct tgtctgttga agcagacaaa gctgccaagc gtgctgttgt ggttggctgt     240 ggtgaaagt tcccagttga agatgccaaa gaggaagtcc agctcttcct tgggaatgct     300
gggattgcca tgagatcctt gactgcagct gtcactgcag ctggtgggaa tgccacctat     360
gttcttgatg gcgtgccacg catgaggggag agacccattg gcgacttggt ggttggcttg     420
aagcaacttg gagctgatgt tgactgcttc cttggcaccg actgtccacc tgttcgtgtc     480
aatgggattg gaggtctccc tggtggcaag gtcaagctct ctggctccat cagctcccag     540
tacttgtcag ccttgctcat ggcagctccc ttggctcttg gtgatgtgga gattgagatc     600
attgacaaac tcatctccat tccctatgtg gagatgacct tgagattgat ggaaaggttt     660
ggtgtgaaag ctgagcattc tgacagctgg gacagattct acatcaaggg aggtcagaag     720
tacaagtcac ccaagaatgc ctatgttgaa ggtgatgcca gctctgccag ctacttcttg     780
gctggtgctg caatcactgg agggactgtg acagtggaag gttgtggcac taccagcttg     840
caaggtgatg tgaagtttgc tgaggtgctt gagatgatgg gagcaaaggt cacctggact     900
gaaacctccg tcacagtgac tggacctcca agggagccat cggaaggaa acatctcaaa     960 gccattgatg tcaacatgaa caagatgcca gatgttgcca tgactcttgc tgtggttgca    1020
ctctttgccg atggaccaac agccatcaga gatgtggctt cctggagagt caaggagaca    1080
gagaggatgg ttgcaatacg cacagagttg accaaacttg agccagcgt tgaggaagga    1140 ccagactact gcatcatcac acctcccgag aagctcaacg tgacagccat agacaccctat    1200 gatgaccacc gcatggcaat ggctttctcc cttgcagcct gtgcagaagt ccctgtcacc    1260
atacgtgacc ctgggtgcac tcgcaagacc ttcccagact actttgatgt gctcagcacc    1320
```

```
tttgtcaaga actga                                                      1335

<210> SEQ ID NO 6
<211> LENGTH: 1338
<212> TYPE: DNA
<213> ORGANISM: Zea mays
<220> FEATURE:
<221> NAME/KEY: CDS
<222> LOCATION: (4)..(1335)

<400> SEQUENCE: 6 atg gcg ggt gcc gag gag atc gtg ctg cag ccc atc aag gag atc tcc    48
    Ala Gly Ala Glu Glu Ile Val Leu Gln Pro Ile Lys Glu Ile Ser
    1               5                  10                  15 ggc acc gtc aag ctg ccg ggg tcc aag tcg ctt tcc aac cgg atc ctc    96
Gly Thr Val Lys Leu Pro Gly Ser Lys Ser Leu Ser Asn Arg Ile Leu
                20                  25                  30 cta ctc gcc gcc ctg tcc gag ggg aca aca gtg gtt gat aac ctg ctg   144
Leu Leu Ala Ala Leu Ser Glu Gly Thr Thr Val Val Asp Asn Leu Leu
            35                  40                  45 aac agt gag gat gtc cac tac atg ctc ggg gcc ttg agg act ctt ggt   192
Asn Ser Glu Asp Val His Tyr Met Leu Gly Ala Leu Arg Thr Leu Gly
        50                  55                  60 ctc tct gtc gaa gcg gac aaa gct gcc aaa aga gct gta gtt gtt ggc   240
Leu Ser Val Glu Ala Asp Lys Ala Ala Lys Arg Ala Val Val Val Gly
65                  70                  75 tgt ggt gga aag ttc cca gtt gag gat gct aaa gag gaa gtg cag ctc   288
Cys Gly Gly Lys Phe Pro Val Glu Asp Ala Lys Glu Glu Val Gln Leu
80                  85                  90                  95 ttc ttg ggg aat gct gga act gca atg cgg cca ttg aca gca gct gtt   336
Phe Leu Gly Asn Ala Gly Thr Ala Met Arg Pro Leu Thr Ala Ala Val
                100                 105                 110 act gct gct ggt gga aat gca act tac gtg ctt gat gga gta cca aga   384
Thr Ala Ala Gly Gly Asn Ala Thr Tyr Val Leu Asp Gly Val Pro Arg
            115                 120                 125 atg agg gag aga ccc att ggc gac ttg gtt gtc gga ttg aag cag ctt   432
Met Arg Glu Arg Pro Ile Gly Asp Leu Val Val Gly Leu Lys Gln Leu
        130                 135                 140 ggt gca gat gtt gat tgt ttc ctt ggc act gac tgc cca cct gtt cgt   480
Gly Ala Asp Val Asp Cys Phe Leu Gly Thr Asp Cys Pro Pro Val Arg
    145                 150                 155 gtc aat gga atc gga ggg cta cct ggt ggc aag gtc aag ctg tct ggc   528
Val Asn Gly Ile Gly Gly Leu Pro Gly Gly Lys Val Lys Leu Ser Gly
160                 165                 170                 175 tcc atc agc agt cag tac ttg agt gcc ttg ctg atg gct gct cct ttg   576
Ser Ile Ser Ser Gln Tyr Leu Ser Ala Leu Leu Met Ala Ala Pro Leu
                180                 185                 190 gct ctt ggg gat gtg gag att gaa atc att gat aaa tta atc tcc att   624
Ala Leu Gly Asp Val Glu Ile Glu Ile Ile Asp Lys Leu Ile Ser Ile
            195                 200                 205 ccg tac gtc gaa atg aca ttg aga ttg atg gag cgt ttt ggt gtg aaa   672
Pro Tyr Val Glu Met Thr Leu Arg Leu Met Glu Arg Phe Gly Val Lys
        210                 215                 220 gca gag cat tct gat agc tgg gac aga ttc tac att aag gga ggt caa   720
Ala Glu His Ser Asp Ser Trp Asp Arg Phe Tyr Ile Lys Gly Gly Gln
    225                 230                 235 aaa tac aag tcc cct aaa aat gcc tat gtt gaa ggt gat gcc tca agc   768
Lys Tyr Lys Ser Pro Lys Asn Ala Tyr Val Glu Gly Asp Ala Ser Ser
240                 245                 250                 255 gca agc tat ttc ttg gct ggt gct gca att act gga ggg act gtg act   816
Ala Ser Tyr Phe Leu Ala Gly Ala Ala Ile Thr Gly Gly Thr Val Thr
```

```
Ala Ser Tyr Phe Leu Ala Gly Ala Ala Ile Thr Gly Gly Thr Val Thr
            260                 265                 270 gtg gaa ggt tgt ggc acc act agt ttg cag ggt gat gtg aag ttt gct      864
Val Glu Gly Cys Gly Thr Thr Ser Leu Gln Gly Asp Val Lys Phe Ala
            275                 280                 285 gag gta ctg gag atg atg gga gcg aag gtt aca tgg acc gag act agc      912
Glu Val Leu Glu Met Met Gly Ala Lys Val Thr Trp Thr Glu Thr Ser
            290                 295                 300 gta act gtt act ggc cca ccg cgg gag cca ttt ggg agg aaa cac ctc      960
Val Thr Val Thr Gly Pro Pro Arg Glu Pro Phe Gly Arg Lys His Leu
305                 310                 315 aag gcg att gat gtc aac atg aac aag atg cct gat gtc gcc atg act     1008
Lys Ala Ile Asp Val Asn Met Asn Lys Met Pro Asp Val Ala Met Thr
320                 325                 330                 335 ctt gct gtg gtt gcc ctc ttt gcc gat ggc ccg aca gcc atc aga gac     1056
Leu Ala Val Val Ala Leu Phe Ala Asp Gly Pro Thr Ala Ile Arg Asp
                340                 345                 350 gtg gct tcc tgg aga gta aag gag acc gag agg atg gtt gcg atc cgg     1104
Val Ala Ser Trp Arg Val Lys Glu Thr Glu Arg Met Val Ala Ile Arg
            355                 360                 365 acg gag cta acc aag ctg gga gca tct gtt gag gaa ggg ccg gac tac     1152
Thr Glu Leu Thr Lys Leu Gly Ala Ser Val Glu Glu Gly Pro Asp Tyr
        370                 375                 380 tgc atc atc acg ccg ccg gag aag ctg aac gtg acg gcg atc gac acg     1200
Cys Ile Ile Thr Pro Pro Glu Lys Leu Asn Val Thr Ala Ile Asp Thr
385                 390                 395 tac gac gac cac agg atg gcc atg gcc ttc tcc ctt gcc gcc tgt gcc     1248
Tyr Asp Asp His Arg Met Ala Met Ala Phe Ser Leu Ala Ala Cys Ala
400                 405                 410                 415 gag gtc ccc gtc acc atc cgg gac cct ggg tgc acc cgg aag acc ttc     1296
Glu Val Pro Val Thr Ile Arg Asp Pro Gly Cys Thr Arg Lys Thr Phe
                420                 425                 430 ccc gac tac ttc gat gtg ctg agc act ttc gtc aag aat taa             1338
Pro Asp Tyr Phe Asp Val Leu Ser Thr Phe Val Lys Asn
            435                 440

<210> SEQ ID NO 7
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggctggag ctgaagagat tgtgctccaa cccatcaagg agatctctgg cacagtcaaa       60
ctccctggct caaagtcact ttcaaaccgt atcctcttgc ttgcagctct ttctgaaggg      120
accacagtgg ttgacaacct tctcaactca gaggatgtcc actacatgct cggagccttg      180
aggactcttg gcttgtctgt tgaagcagac aaagctgcca gcgtgctgt tgtggttggc      240 tgtggtggaa agttcccagt tgaagatgcc aaagaggaag tccagctctt ccttgggaat      300
gctgggattg ccatgagatc cttgactgca gctgtcactg cagctggtgg aatgccacc       360 tatgttcttg atggcgtgcc acgcatgagg gagagaccca ttgcgacttt ggtggttggc      420
ttgaagcaac ttggagctga tgttgactgc ttccttggca ccgactgtcc acctgttcgt      480
gtcaatggga ttggaggtct ccctggtggc aaggtcaagc tctctggctc catcagctcc      540
cagtacttgt cagccttgct catggcagct cccttggctc ttggtgatgt ggagattgag      600
atcattgaca aactcatctc cattccctat gtggagatga ccttgagatt gatggaaagg      660
```

```
tttggtgtga aagctgagca ttctgacagc tgggacagat tctacatcaa gggaggtcag    720
aagtacaagt cacccaagaa tgcctatgtt gaaggtgatg ccagctctgc cagctacttc    780
ttggctggtg ctgcaatcac tggagggact gtgacagtgg aaggttgtgg cactaccagc    840
ttgcaaggtg atgtgaagtt tgctgaggtg cttgagatga tgggagcaaa ggtcacctgg    900
actgaaacct ccgtcacagt gactggacct ccaagggagc cattcggaag gaaacatctc    960
aaagccattg atgtcaacat gaacaagatg ccagatgttg ccatgactct tgctgtggtt   1020
gcactctttg ccgatggacc aacagccatc agagatgtgg cttcctggag agtcaaggag   1080
acagagagga tggttgcaat acgcacagag ttgaccaaac ttggagccag cgttgaggaa   1140
ggaccagact actgcatcat cacacctccc gagaagctca acgtgacagc catagacacc   1200
tatgatgacc accgcatggc aatggctttc tcccttgcag cctgtgcaga agtccctgtc   1260
accatacgtg accctgggtg cactcgcaag accttcccag actactttga tgtgctcagc   1320
acctttgtca agaactga                                                 1338
```

OPTIMIZED EXPRESSION OF GLYPHOSATE RESISTANCE ENCODING NUCLEIC ACID MOLECULES IN PLANT CELLS

REFERENCE TO RELATE APPLICATION

This application claims priority to previously filed and co-pending provisional application U.S. Ser. No. 61/419,703, the contents of which are incorporate herein by reference in their entirety.

SEQUENCE LISTING

The instant application contains a Sequence Listing which has been submitted in ASCII format via EFS-Web and is hereby incorporated by reference in its entirety. Said ASCII copy, created on Nov. 22, 2011, is named 210007PCT.txt and is 26,865 bytes in size.

BACKGROUND OF THE INVENTION

Glyphosate (N-phosphonomethylglycine) is a widely used component in herbicides. Glyphosate inhibits 5-enolpyruvyl-3-phosphoshikimic acid synthase (EPSP synthase, or EPSPS). 5-enolpyruvyl-3-phosphoshikimic acid synthase is involved in the synthesis of aromatic amino acids in plant cells. Inhibition of EPSPS effectively disrupts protein synthesis and thereby kills the affected plant cells. Because glyphosate is non-selective, it kills both weeds and crop plants. Thus it is useful with crop plants when one can modify the crop plants to be resistant to glyphosate, allowing the desirable plants to survive exposure to the glyphosate.

Recombinant DNA technology has been used to isolate mutant EPSP synthases that are glyphosate-resistant. Such glyphosate-resistant mutant EPSP synthases can be transformed into plants and confer glyphosate-resistance upon the transformed plants. By way of example, a glyphosate tolerant gene was isolated from *Agrobacterium* strain CP4 as described in U.S. Pat. No. 5,633,435. The full length maize EPSPS gene is described at U.S. Pat. No. 7,045,684. It is imported to the chloroplast and the chloroplast transit peptide cleaved, producing the mature EPSPS. See Herouet-Guicheney et al. (2009) "Safety evaluation of the double mutant 5-enolypyruvylshikimate-3-phosphate synthase (2mEPSPS) from maize that confers tolerance to glyphosate herbicide in transgenic plants" Regulatory Toxicology and Pharmacology, Vol. 54, Issue 2, pp 143-153. This reference and all references cited are incorporated herein by reference.

Other glyphosate tolerant genes have been created through the introduction of mutations. These include those isolated by Comai and described at U.S. Pat. Nos. 5,094,945, 4,769,061 and 4,535,060. A single mutant has been utilized, as described in U.S. Pat. No. 5,310,667 by substituting an alanine residue for a glycine residue at between positions 80 and 120. Double mutants are also described at U.S. Pat. Nos. 6,225,114 and 5,866,775 in which, in addition to the above mutation, a second mutation (a threonine residue for an alanine residue between positions 170 and 210) is introduced into a wild-type EPSPS gene.

Other work resulted in the production of a double mutant EPSPS maize through the introduction of a modified maize EPSPS gene bearing mutations at residue 102 (changing threonine to isoleucine) and at residue 106 (changing proline to serine) of the amino acid sequence encoded by GenBank Accession No. X63374 and shown in U.S. Pat. Nos. 6,566, 587 and 6,040,497, each of which are incorporated herein by reference in their entirety.

SUMMARY OF THE INVENTION

The invention is directed to a codon optimized modified EPSPS sequence which, when expressed in a plant, confers resistance or tolerance to a glyphosate herbicide. The nucleotide sequence is optimized for expression in plants, preferably for expression in both dicotyledonous and monocotyledonous plants, and most preferably in soybean (*Glycine max*) plants. The amino acid encoded contains two mutations when compared to the wild-type EPSPS polypeptide, of threonine to isoleucine at corresponding residue 102 and proline to serine at corresponding residue 106 when compared to the wild-type *Zea mays* EPSPS polypeptide.

BRIEF DESCRIPTION OF THE DRAWINGS

FIG. 1 is the sequence as set forth in Genbank accession number X63374, which is the wild-type maize (*Zea mays*) EPSPS nucleotide sequence coding for the predicted mature maize EPSPS sequence following import and cleavage of the optimized chloroplast transit peptide and is SEQ ID NO: 1; below the nucleotide sequence is indicated the encoded amino acid sequence of the predicted mature maize EPSPS which is SEQ ID NO: 2. Residues 102 and 106 are in bold and underlined; substitution of isoleucine for threonine at 102 and substitution of serine for proline at position 106 of the protein is the double mutant maize EPSPS protein (2mEPSPS) and is SEQ ID NO: 3. FIG. 1 discloses the full-length sequence, including the "atg" start codon as SEQ ID NO: 6.

FIG. 2 shows the nucleotide sequence of a Double Mutant Maize EPSPS Gene (2mEPSPS v1) and is SEQ ID NO: 4. The ATG start codon site is in italics.

FIG. 3 shows the optimized Double Mutant Maize EPSPS Gene (2mEPSPS v2) nucleic acid molecule and is SEQ ID NO: 5. FIG. 3 discloses the full-length sequence, including the "atg" start codon as SEQ ID NO: 7.

FIG. 4A-B shows an alignment of the *Zea mays* 2mEPSPS v1 nucleic acid molecule (SEQ ID NO: 4) and the optimized DMMG nucleic acid molecule (2mEPSPS v2, SEQ ID NO: 7).

BRIEF DESCRIPTION OF THE SEQUENCES

Figure 5:
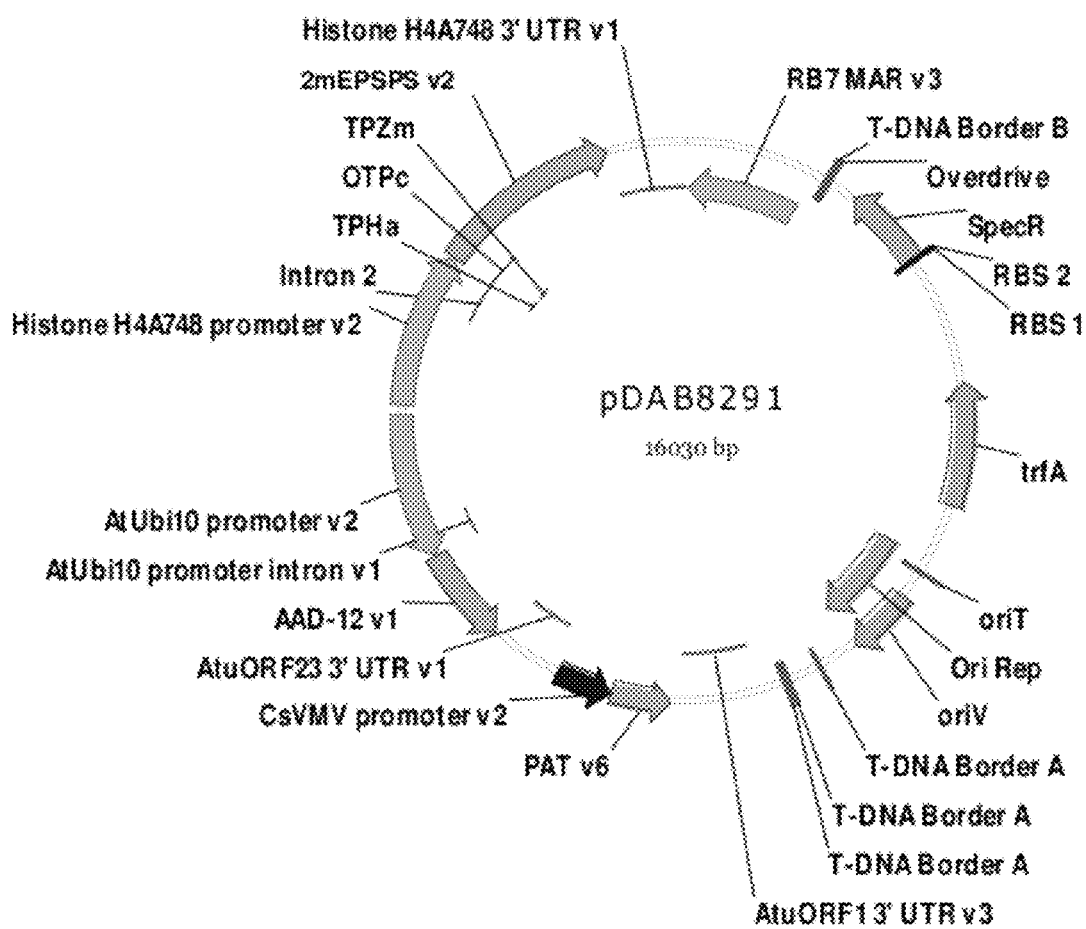
FIG. 5 is a plasmid map of construct pDAB8291.

SEQ ID NO: 1: is X63374 maize EPSPS wildtype nucleotide sequence (coding for the predicted mature wildtype EPSPS)

SEQ ID NO: 2: is predicted mature wildtype EPSPS amino acid sequence from X63374 SEQ ID NO: 3: is predicted 2mEPSPS double mutant amino acid sequence.

SEQ ID NO: 4: is maize native sequence nucleotide sequence 2mEPSPS v1 coding for double mutant 2mEPSPS SEQ ID NO: 5: is hemicot optimized sequence nucleotide sequence 2mEPSPS v2 coding for double mutant 2mEPSPS

DETAILED DESCRIPTION OF EMBODIMENTS OF THE INVENTION

To obtain high expression of heterologous genes in plants it may be preferred to reengineer said genes so that they are more efficiently expressed in plant cells, and in particular may be preferred where a monocotyledonous gene is desired to be expressed in both dicotyledonous as well as monocotyledonous plant cells. The wild-type gene encoding 5-enolpyruvyl-3-phosphoshikimic acid synthase (EPSPS) has been isolated and the Zea mays nucleotide sequence coding for the predicted mature maize EPSPS sequence following import and cleavage of the optimized chloroplast transit peptide can be found at GenBank accession number X63374, also shown in U.S. Pat. No. 6,566,587, (particularly sequence identifier number 3 there) and which is incorporated herein by reference in its entirety. Here the sequence is SEQ ID NO: 1, also shown in FIG. 1. In FIG. 1, below the wild-type EPSPS nucleotide sequence is indicated the encoded wild-type amino acid sequence which is SEQ ID NO: 2. Glyphosate (N-phosphonomethylglycine) is a widely used component in herbicides. Glyphosate inhibits EPSPS, which is involved in the synthesis of aromatic amino acids in plant cells. Inhibition of EPSPS effectively disrupts protein synthesis and thereby kills the affected plant cells. Providing a plant or plant cell that is resistant to glyphosate can be useful in a variety of applications, where those plant cells having such resistance can tolerate exposure to glyphosate. Modification of the wild-type plant EPSPS nucleotide sequence can provide such resistance when expressed in a plant cell. Referring to FIG. 1, and as described in the '587 patent, when comparing an EPSPS polypeptide to the wild-type polypeptide of FIG. 1, modification to substitute isoleucine for threonine at residue 102 and substitute serine for proline at position 106 of the protein (both positions indicated in bold and underlined in FIG. 1) the result is the double mutant EPSPS polypeptide (2mEPSPS), here SEQ ID NO: 3. When expressed in a plant cell with the appropriate chloroplast transit peptide, it provides tolerance to glyphosate following import into the chloroplast and processing to the mature enzyme form (FIG. 1).

Here, design of a gene 2mEPSPS v2 for expression of the same 2mEPSPS protein in both monocotyledonous and dicotyledonous plants is shown with a reengineering of the protein coding region of this gene for optimal expression. Described here is an optimized nucleotide sequence encoding a 5-enolpyruvyl-3-phosphoshikimic acid synthase (EPSP synthase, or EPSPS) polypeptide which is modified from the wild-type EPSPS polypeptide.

A double mutant nucleotide sequence from Zea mays that is 1338 base pairs is shown in FIG. 2 and is SEQ ID NO: 4. This modified nucleotide sequence is referred to as a double mutant maize gene or DMMG and provides tolerance to glyphosate. This is a Zea mays 2mEPSPS nucleotide sequence also referred to as 2mEPSPS v1. It encodes the 2mEPSPS polypeptide of SEQ ID NO: 3, which contains the substitution of isoleucine for threonine at residue 102 and serine for proline at residue 106 compared to the wild-type EPSPS polypeptide of SEQ ID NO: 2.

The 2mEPSPS v1 nucleic acid molecule of SEQ ID NO: 4 was optimized to improve expression in both dicotyledonous plants as well as monocotyledonous plants, and in particular in soybean. Codon usage was selected based upon preferred hemicot codon usage in that it was redesigned such that the protein is encoded by codons having a bias toward both monocot and dicot plant usage, and deleterious sequences and superfluous restriction sites were removed to increase the efficiency of transcription/translation of the DMMG coding sequence and to facilitate DNA manipulation steps. In doing so, expression of 2mEPSPS in dicotyledonous plants and soybean in particular provides resistance to glyphosate application.

The optimized sequence is shown in FIG. 3, (SEQ ID NO: 5). The ATG start site is in italics and indicated above the optimized sequence of SEQ ID NO: 5 (full-length sequence including "atg" start codon is disclosed as SEQ ID NO: 7). Both the optimized sequence and the mutant Zea mays sequence encode the same 2mEPSPS protein, that is shown in SEQ ID NO: 3.

A nucleotide sequence alignment of the monocotyledonous and dicotyledonous plant optimized 2mEPSPS v2 DNA sequence as compared to the native maize codon 2mEPSPS v1 DNA sequence from Zea mays (SEQ ID NO:4) is displayed in FIG. 4. Although the 2mEPSPS protein sequences are 100% identical at the amino acid level, they are gene versions 1 and 2 only 85.5% identical at the nucleotide level. The resulting divergence is a result of the codon selections which were made using the strategy described above.

The optimized 2mEPSPS v2 nucleic acid molecule is useful in a wide variety of applications in which glyphosate resistance can be of use in the plant. Glyphosate, sulfosate and fosametine are broad-spectrum systemic herbicides of the phosphonomethylglycine family. When referring to glyphosate, the term should be considered to include any herbicidally effective form of N-phosphonomethylglycine and any salt thereof and forms which result in the production of the glyphosate zwitterion in planta. Glyphosate is a competitive inhibitors of 5-enolpyruvylshikimate-3-phosphate synthase (EC 2.5.1.19) or EPSPS with respect to the binding of PEP (phosphoenolpyruvate). After the application of phosphonomethylglycine herbicide to the plant, it is translocated in the plant where it accumulates in the rapidly growing parts, in particular the cauline and root apices, causing damage to the point of destruction of sensitive plants. Depending upon the application rate of the herbicide, the sensitive plant growth is inhibited, that is, its growth is slowed or stopped completely. The tolerance of plants to glyphosate and to products of the family is obtained by stable introduction into their genome of such an optimized modified EPSPS. It is known, for example from U.S. Pat. Nos. 4,535,060 and 6,566,587, to confer on a plant a tolerance to a herbicide of the above type, especially N-phosphonomethylglycine or glyphosate, by introducing into the genome of plants a gene coding for an EPSPS carrying a mutation that makes this enzyme more resistant to its competitive inhibitor (glyphosate) after localization of the enzyme in the plastid compartment. When referring to resistance or tolerance to the glyphosate herbicide, it is meant that any impact of the herbicide on the plant does not kill the plant; there can be minimal impact on the plant or no impact at all, such that such that any adverse impact on the plant comprising the heterologous nucleic acid molecule providing resistance or tolerance is less than in a plant not comprising a nucleic acid molecule providing resistance or tolerance to glyphosate.

Such a nucleic acid molecule is particularly useful when expressed in *Glycine max*, soybean plants. The nucleic acid molecule may be isolated from any host and modified so that it comprises the nucleic acid molecule of the invention, may be isolated from *Zea mays* or soybean or other plant, isolated from a microbe, or may be synthetically produced; the method of producing the nucleic acid molecule of the invention is not critical.

As used herein, the terms nucleic acid or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequence.

Deoxyribonucleic acid (DNA) is a polymer comprising four mononucleotide units, (D)dAMP (2'-(D) deoxyadenosine-5-monophosphate), dGMP (2'-(D)deoxyguanosine-5-monophosphate), dCMP (2'-(D)deoxycytosine-5-monophosphate) and dTMP (2'-(D)deoxycytosine-5-monophosphate) linked in various sequences by 3',5'-phosphodiester bridges. The structural DNA consists of multiple nucleotide triplets called "codons" which code for the amino acids. The codons correspond to the various amino acids as follows: Arg (CGA, CGC, CGG, CGT, AGA, AGG); Leu (CTA, CTC, CTG, CTT, TTA, TTG); Ser (TCA, TCC, TCG, TCT, AGC, AGT); Thr (ACA, ACC, ACG, ACT); Pro (CCA, CCC, CCG, CCT); Ala (GCA, GCC, GCG, GCT); Gly (GGA, GGC, GGG, GGT); Ile (ATA, ATC, ATT); Val (GTA, GTC, GTG, GTT); Lys (AAA, AAG); Asn (AAC, AAT); Gln (GAA, CAG); His (CAC, CAT); Glu (GAA, GAG); Asp (GAC, GAT); Tyr (TAC, TAT); Cys (TGC, TGT); Phe (TTC, TTT); Met (ATG); and Trp (UGG). Moreover, due to the redundancy of the genetic code (i.e., more than one codon for all but two amino acids), there are many possible DNA sequences which may code for a particular amino acid sequence.

In the amino acid sequences discussed here, the standard single letter or three letter nomenclature are used. All peptide structures represented in the following description are shown in conventional format in which the amino group at the N-terminus appears to the left and the carboxyl group at the C-terminus at the right Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser; S), threonine (Thr,T), tryptophan (Trp;W), tyrosine (Tyr;Y), and valine (Val;V). An "X" may be used when the amino acid residue is unknown and parentheses designate that an unambiguous assignment is not possible and the amino acid designation within the parentheses is the most probable estimate based on known information.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, plasmid DNA fragments, cDNA fragments, RNA fragments, PCR amplified DNA fragments, oligonucleotides, or other polynucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 0.1% SDS (sodium dodecyl sulfate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995).

Specificity is also the function of post-hybridization washes, the critical factors being the ionic strength and temperature of the final wash solution. For DNA-DNA hybrids, the $T_m$ can be approximated from the equation $T_m=81.5°$ C.$+16.6(\log M)+0.41(\% GC)-0.61(\% form.)-500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al, *Short Protocols in Molecular Biology*, page 2-40, Third Edit. (1997) and Sambrook et al. (1989).

In general, sequences that correspond to the nucleotide sequences of the present invention and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MEG-ALIGN, and SAM sequence alignment computer programs; or, by manual visual inspection.

Another example of algorithm that is suitable for determining sequence similarity is the BLAST algorithm, which is described in Altschul et al, J. Mol. Biol. 215: 403-410 (1990). The BLAST programs (Basic Local Alignment Search Tool) of Altschul, S. F., et al., (1993) J. Mol. Biol. 215:403-410) searches under default parameters for identity to sequences contained in the BLAST "GENEMBL" database. A sequence can be analyzed for identity to all publicly available DNA sequences contained in the GENEMBL database using the BLAS TN algorithm under the default parameters.

Software for performing BLAST analyses is publicly available through the National Center for Biotechnology Information,www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff, Proc. Natl. Acad. Sci. USA 89:10915-10919 (1992)) alignments (B) of 50, expectation (E) of 10, M=5, N=−4, and a comparison of both strands. The term BLAST refers to the BLAST algorithm which performs a statistical analysis of the similarity between two sequences; see, e.g., Karlin, Proc. Natl. Acad. Sci. USA 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (J. Mol. Biol. 48:443-453, 1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff, Proteins, 17: 49-61 (1993)), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) Proc. Natl. Acad. Sci. USA 89:10915).

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

Various assays can be employed in connection with the nucleic acid molecule of the invention. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ (or other probe labels) and washed in an SDS solution. In the Western analysis, instead of isolating DNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997); Towbin et al, (1979) "Electrophoretic transfer of proteins from polyacrylamide gels to nitrocellulose sheets: procedure and some applications" Proc Natl Acad Sci USA 76(9): 4350-4354; Renart et al. "Transfer of proteins from gels to diazobenzyloxymethyl-paper and detection with antisera: a method for studying antibody specificity and antigen structure" Proc Natl Acad Sci USA 76(7): 3116-3120. In Northern analysis, RNA is isolated and analyzed.

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate The foregoing techniques are useful in a variety of situations, and in one embodiment, are useful in detecting the presence of the nucleic acid molecule and/or the polypeptide encoded in a plant cell. For example, the presence of the molecule can be determined in a variety of ways, including using a primer or probe of the sequence, ELISA assay to detect the encoded protein, a Western blot to detect the protein, Northern or Southern blot to detect RNA or DNA, and/or isolating a sequence and determining percent identity to the nucleic acid molecule or detecting presence of an operably linked marker. Further, an antibody which can detect the presence of the double mutant EPSPS protein is disclosed at U.S. Pat. No. 7,807,791, incorporated herein by reference.

The term introduced in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poelman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The expression cassette can include one or more enhancers in addition to the promoter. Enhancer is intended to mean a cis-acting sequence that increases the utilization of a promoter. Such enhancers can be native to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938.

The term plant is used broadly herein to include a plant at any stage of development, or part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, the present invention provides plants regenerated from the tissue cultures of the invention.

A construct is a package of genetic material inserted into the genome of a cell via various techniques.

As used herein, the term vector refers broadly to any plasmid or virus encoding an exogenous nucleic acid. An example of a vector commonly used in plant molecular biology is the binary vector which can be engineered to contain a construct, see Bevan M., (1984) Nucl. Acids Res., 12 (22): 8711-8721. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989. *Molecular Cloning: A Laboratory Manual*, 2$^{nd}$ Edition. Cold Spring Harbor Laboratory Press, Plainview, N.Y.).

In the methods of the invention, a number of promoters that direct expression of a gene in a plant can be employed. Such promoters can be selected from constitutive, chemically-regulated, inducible, tissue-specific, and seed-preferred promoters. Constitutive promoters include, for example, the core CaMV 35S promoter (Odell et al. (1985) Nature 313:810-812); rice actin (McElroy et al. (1990) Plant Cell 2:163-171); Maize ubiquitin (U.S. Pat. No. 5,510,474; Christensen et al. (1989) Plant Mol. Biol. 12:619-632 and Christensen et al. (1992) Plant Mol. Biol. 18:675-689); pEMU (Last et al.

(1991) Theor. Appl. Genet. 81:581-588); MAS (Velten et al. (1984) EMBO J. 3:2723-2730), the core promoter of the Rsyn7 promoter and other constitutive promoters disclosed in WO 99/43838 and U.S. Pat. No. 6,072,050; rice actin (McElroy et al. (1990) Plant Cell 2:163-171); pEMU (Last et al. (1991) Theor. Appl. Genet. 81:581-588); MAS (Velten et al. (1984) EMBO J. 3:2723-2730); ALS promoter (U.S. Pat. No. 5,659,026); rice actin promoter (U.S. Pat. No. 5,641,876; WO 00/70067), maize histone promoter (Chaboute et al. Plant Molecular Biology, 8:179-191 (1987), Brignon et al., Plant Mol Bio 22(6):1007-1015 (1993); Rasco-Gaunt et al., Plant Cell Rep. 21(6):569-576 (2003)) and the like. Other constitutive promoters include, for example, U.S. Pat. Nos. 5,608,149; 5,608,144; 5,604,121; 5,569,597; 5,466,785; 5,399,680; 5,268,463; and 5,608,142.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the instant invention. See Ward et al. Plant Mol. Biol. 22: 361-366 (1993). Exemplary inducible promoters include ecdysone receptor promoters, U.S. Pat. No. 6,504,082; promoters from the ACE1 system which responds to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)) Tet repressor from Tn10 (Gatz et al., Mol. Gen. Genet. 227: 229-237 (1991); or from a steroid hormone gene, the transcriptional activity of which is induced by a glucocorticosteroid hormone. Schena et al., Proc. Natl. Acad. Sci. U.S.A. 88: 10421 (1991); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2): 247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156).

A cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as P5CS (Zang et al. (1997) Plant Sciences 129:81-89); cold-inducible promoters, such as, cor15a (Hajela et al. (1990) Plant Physiol. 93:1246-1252), cor15b (Wlihelm et al. (1993) Plant Mol Biol 23:1073-1077), wsc120 (Ouellet et al. (1998) FEBS Lett. 423-324-328), ci7 (Kirch et al. (1997) Plant Mol. Biol. 33:897-909), ci21A (Schneider et al. (1997) Plant Physiol. 113:335-45); drought-inducible promoters, such as, Trg-31 (Chaudhary et al (1996) Plant Mol. Biol. 30:1247-57), rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); and heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the *Agrobacterium* pmas promoter (Guevara-Garcia et al. (1993) Plant J. 4(3):495-505) and the *Agrobacterium* ORF13 promoter (Hansen et al., (1997) Mol. Gen. Genet. 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these type of promoters include seed preferred expression such as that provided by the phaseolin promoter (Bustos et al.1989. *The Plant Cell* Vol. 1, 839-853), and the maize globulin-1 gene, Belanger, et al. 1991 *Genetics* 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. Plant J. 4: 567-577), the P-gene promoter from corn (Chopra et al. 1996. Alleles of the maize P gene with distinct tissue specificities encode Myb-homologous proteins with C-terminal replacements. Plant Cell 7:1149-1158, Erratum in Plant Cel. 1997, 1:109), the globulin-1 promoter from corn (Belenger and Kriz. 1991. Molecular basis for Allelic Polymorphism of the maize Globulin-1 gene. Genetics 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase$_{1-2}$ Gene Capable of Conferring Tissue-Specific Gene Expression in Transgenic Maize. Plant Science 163:865-872), GenBank accession number AF359511.

Other components of the vector may be included, also depending upon intended use of the gene. Examples include selectable markers, targeting or regulatory sequences, transit peptide sequences such as the optimized transit peptide sequence (see, U.S. Pat. No. 5,510,471) stabilizing sequences such as RB7MAR (see, Thompson and Myatt, (1997) *Plant Mol. Biol.*, 34: 687-692 and WO9727207) or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp 7831-7846(nos)). See also, Guerineau et al. Mol. Gen. Genet. 262:141-144 (1991); Proudfoot, *Cell* 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al. Nucleic Acids Res. 17:7891-7903 (1989); Joshi et al. Nucleic Acid Res. 15:9627-9639 (1987).

Reporter or marker genes for selection of transformed cells or tissues or plant parts or plants can be included in the transformation vectors. Examples of selectable markers include those that confer resistance to antimetabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, 1983; Meijer et al., Plant Mol. Biol. 16:807-820, 1991); neomycin phosphotransferase, which confers resistance to the aminoglycosides neomycin, kanamycin and paromycin (Herrera-Estrella, EMBO J. 2:987-995, 1983 and Fraley et al. Proc. Natl. Acad. Sci. USA 80:4803 (1983)) and hygromycin phosphotransferase, which confers resistance to hygromycin (Marsh, Gene 32:481-485, 1984; see also Waldron et al., Plant Mol. Biol. 5:103-108, 1985; Zhijian et al., Plant Science 108:219-227, 1995); trpB, which allows cells to utilize indole in place of tryptophan; hisD, which allows cells to utilize histinol in place of histidine (Hartman, Proc. Natl. Acad. Sci., USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, Biosci. Biotechnol. Biochem. 59:2336-2338, 1995). Additional selectable markers include, for example, a mutant EPSP-synthase, which confers glyphosate resistance (Hinchee et al., BioTechnology 91:915-922, 1998), a mutant acetolactate synthase, which confers imidazolinone or sulfonylurea resistance (Lee et al., EMBO J. 7:1241-1248, 1988), a mutant psbA, which confers resistance to atrazine (Smeda et al., Plant Physiol. 103:911-917, 1993), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, 1983); streptomycin (Jones et al., Mol. Gen. Genet. 210:86-91, 1987); spectinomycin (Bretagne-Sagnard et al., Transgenic Res. 5:131-137, 1996); bleomycin (Hille et al., Plant Mol. Biol. 7:171-176, 1990); sulfonamide (Guerineau et al., Plant Mol. Biol. 15:127-136, 1990); bromoxynil (Stalker et al., Science 242:419-423, 1988); glyphosate (Shaw et al., Science 233:478-481, 1986); phosphinothricin (DeBlock et al., EMBO J. 6:2513-2518, 1987), and the like. One option for use of a selective gene is a glufosinate-resistance encoding DNA and in one embodiment can be the phosphinothricin acetyl transferase (PAT), maize optimized PAT gene or bar gene under the control of the CaMV 35S or ubiquitin promoters. The genes confer resistance to bialaphos. (see, Wohlleben et al., (1988) *Gene* 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the PAT gene is the maize optimized PAT gene, described at U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); alkaline phosphatase. In a preferred embodiment, the marker used is beta-carotene or provitamen A (Ye et al, Science 287:303-305—(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein is needed. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize $C_1$ gene (Kao et al., Plant Cell (1996) δ: 1171-1179;

Scheffler et al. Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al, Proc. Natl. Acad. Sci. USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others. Yet further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PHIYFP™ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al. (2002) Biotechniques 2(2): 286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129: 2703), which encodes an enzyme capable of oxidizing tyrosine to DOPA and dopaquinone, which in turn condenses to form the easily detectable compound melanin. Clearly, many such markers are available to one skilled in the art.

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al.; Virology 154:9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987).

The construct can also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase and *Heilianthus annus* (see Lebrun et al. U.S. Pat. No. 5,510, 417), *Zea mays* Brittle-1 chloroplast transit peptide (Nelson et al. Plant Physiol 117(4):1235-1252 (1998); Sullivan et al. Plant Cell 3(12):1337-48; Sullivan et al., Planta (1995) 196 (3):477-84; Sullivan et al., J. Biol. Chem. (1992) 267(26): 18999-9004) and the like. In addition chimeric transit peptides are known in the art, such as the Optimized Transit Peptide (see, U.S. Pat. No. 5,510,471). One skilled in the art will readily appreciate the many options available in expressing a product to a particular organelle. For example, the barley alpha amylase sequence is often used to direct expression to the endoplasmic reticulum (Rogers, J. Biol. Chem. 260:3731-3738 (1985)). Use of transit peptides is well known (e.g., see U.S. Pat. Nos. 5,717,084; 5,728,925).

The nucleotide sequence of the invention can be optionally combined with another nucleotide sequence of interest. The term "nucleotide sequence of interest" refers to a nucleic acid molecule (which may also be referred to as a polynucleotide) which can be an RNA molecule as well as DNA molecule, and can be a molecule that encodes for a desired polypeptide or protein, but also may refer to nucleic acid molecules that do not constitute an entire gene, and which do not necessarily encode a polypeptide or protein (e.g., a promoter). For example, the nucleic acid molecule of the invention can be combined or "stacked" with another that provides additional resistance or tolerance to glyphosate or another herbicide, and/or provides resistance to select insects or diseases and/or nutritional enhancements, and/or improved agronomic characteristics, and/or proteins or other produces useful in feed, food, industrial, pharmaceutical or other uses. Stacking of the nucleic acid containing a construct within the plant genome can be accomplished via plant breeding, re-transformation of a transgenic plant, or addition of new traits through targeted integration via homologous recombination.

Such nucleotide sequences include, but are not limited to, those examples provided below:

1. Genes or Coding Sequence (e.g. iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium falvum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B). A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxingenes can be purchased from American Type Culture Collection (Rockville, Md.), under ATCC accession numbers. 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.
(E) An enzyme inhibitor, e.g., a protease inhibitor or an amylase inhibitor. Examples of such genes include, a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor Sumitani et al., 1993 Biosci. Biotech. Biochem. 57:1243).
(F) An insect-specific hormone or pheromone such as an ecdysteroid and juvenile hormone a variant thereof, a mimetic based thereon, or an antagonist or agonist thereof, such as, baculovirus expression of cloned juvenile hormone esterase, an inactivator of juvenile hormone (Hammock et al., 1990 Nature 344:458).
(G) An insect-specific peptide or neuropeptide which, upon expression, disrupts the physiology of the affected pest. J. Biol. Chem. 269:9 Examples of such genes include, an insect diuretic hormone receptor (Regan, 1994), an allostatin identified in *Diploptera punctata* (Pratt, 1989), insect-specific, paralytic neurotoxins (U.S. Pat. No. 5,266,361).
(H) An insect-specific venom produced in nature by a snake, a wasp, etc., such as, a scorpion insectotoxic peptide (Pang, 1992 Gene 116:165).
(I) An enzyme responsible for a hyperaccumulation of monoterpene, a sesquiterpene, a steroid, hydroxamic acid, a phenylpropanoid derivative or another non-protein molecule with insecticidal activity.
(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691) and parsley ubi-4-2 polyubiquitin gene (Kawalleck et al., 1993 Plant Molec. Biol. 21:673).
(K) A molecule that stimulates signal transduction. Examples of such molecules include, nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).
(L) A hydrophobic moment peptide. See U.S. Pat. Nos. 5,659,026 and 5,607,914, the latter teaches synthetic antimicrobial peptides that confer disease resistance.
(M) A membrane permease, a channel former or a channel blocker, such as, a cecropin-β lytic peptide analog (Jaynes et al., 1993 Plant Sci. 89:43) which renders transgenic tobacco plants resistant to *Pseudomonas solanacearum*.
(N) A viral-invasive protein or a complex toxin derived there from. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.
(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.
(P) A virus-specific antibody. See, for example, Tavladoraki et al. (1993) Nature 266:469, which shows that transgenic plants expressing recombinant antibody genes are protected from virus attack.
(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).
(R) A developmental-arrestive protein produced in nature by a plant, such as, the barley ribosome-inactivating gene has an increased resistance to fungal disease (Longemann et al., 1992). Bio/Technology 10:3305
(S) RNA interference in which an RNA molecule is used to inhibit expression of a target gene. An RNA molecule in one example is partially or fully double stranded which triggers a silencing response resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

2. Genes that Confer Resistance to a Herbicide
(A) Genes encoding resistance or tolerance to a herbicide that inhibits the growing point or meristem, such as an imidazalinone or a sulfonylurea. Exemplary genes in this category code for mutant acetolactate synthase (ALS) (Lee et al., 1988 EMBO J. 7:1241) also known as acetohydroxy acid synthase (AHAS) enzyme (Miki et al., 1990 Theor. Appl. Genet. 80:449).
(B) One or more additional genes encoding resistance or tolerance to glyphosate imparted by mutant EPSP synthase and aroA genes, or through metabolic inactivation by genes such as GAT (glyophosate acetyltrasnferase or GOX (glyphosate oxidase) and other phosphono compounds such as glufosinate (PAT and bar genes), and pyridinoxy or phenoxy proprionic acids and cyclohexadiones (ACCase inhibitor encoding genes). See, for example, U.S. Pat. No. 4,940,835, which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to phenoxy proprionic acids and cyclohexadiones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describes the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2-phenyl)propane-1,3-dione, triketones (EP625505, EP625508, U.S. Pat. No. 5,506, 195), in particular sulcotrione, or else pyrazolinates. A gene that produces an overabundance of HPPD in plants can provide tolerance or resistance to such herbicides, including, for example, genes described at U.S. Pat. Nos. 6,268,549 and 6,245,968 and US publication No. 20030066102.

(E) Genes encoding resistance or tolerance to phenoxy auxin herbicides, such as, 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (AAD-1) gene, described at US Publication 20090093366.

(F) Genes encoding resistance or tolerance to phenoxy auxin herbicides, such as, 2,4-dichlorophenoxyacetic acid (2,4-D) and which may also confer resistance or tolerance to pyridyloxy auxin herbicides, such as fluoroxypyr or triclopyr. Examples of such genes include the α-ketoglutarate-dependent dioxygenase enzyme (AAD-12) gene, described at WO 2007/053482 A2.

(G) Genes encoding resistance or tolerance to dicamba (see, e.g., U.S. Patent Publication 20030135879).

(H) Genes providing resistance or tolerance to herbicides that inhibit protoporphyrinogen oxidase (PPO) (see U.S. Pat. No. 5,767,373)

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

3. Genes that Confer or Contribute to a Value-Added Trait
  (A) Modified fatty acid metabolism, for example, by transforming maize or *Brassica* with an antisense gene or stearoyl-ACP desaturase to increase stearic acid content of the plant (Knultzon et al., 1992) Proc. Nat. Acad. Sci. USA 89:2624.

(B) Decreased phytate content
  (1) Introduction of a phytase-encoding gene would enhance breakdown of phytate, adding more free phosphate to the transformed plant, such as the *Aspergillus niger* phytase gene (Van Hartingsveldt et al., 1993 Gene 127:87).
  (2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., 1988) J. Bacteriol. 170:810, *Bacillus subtilis* levansucrase gene (Steinmetz et al., 1985 Mol. Gen. Genel. 200:220), *Bacillus licheniformis* α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:1045).

The nucleotide sequence of interest can also be a nucleotide sequence introduced into a predetermined area of the plant genome through homologous recombination. Methods to integrate a polynucleotide sequence within a specific chromosomal site of a plant cell via homologous recombination have been described within the art. For instance, site specific integration as described in US Patent Application Publication No. 2009/0111188 A1, describes the use of recombinases or integrases to mediate the introduction of a donor polynucleotide sequence into a chromosomal target. In addition, International Patent Application No. WO 2008/021207, describes zinc finger mediated-homologous recombination to integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., Trends in Plant Sci. 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSRi plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

As noted herein, the present invention provides vectors capable of expressing genes of interest. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, Bio/Technology 10:268 (1992); and Weising et al., Ann. Rev. Genet. 22: 421-477 (1988). For example, the DNA construct may be introduced into the genomic DNA of the plant cell using techniques such as microprojectile-mediated delivery, Klein et al., Nature 327: 70-73 (1987) and Tomes et al. Plant Cell, Tissue & Organ Culture: Fundamental Methods, eds. Gambourg and Phillips (1995) (Springer-Velag, Berlin), U.S. Pat. Nos. 4,945,050, 5,879,918 and 5,932,782, for example; electroporation, Fromm et al., Proc. Natl. Acad. Sci. 82: 5824 (1985); polyethylene glycol (PEG) precipitation, Paszkowski et al., EMBO J. 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, Mol. Gen. Genetics 202:179-185 (1985). Co-cultivation of plant tissue with *Agrobacterium tumefaciens* is another option, where the DNA constructs are placed into a binary vector system. See e.g., U.S. Pat. Nos. 5,591,616, 5,563,055 and 5,981,840; Ishida et al., "High Efficiency Transformation of Maize (*Zea mays* L.) mediated by *Agrobacterium tumefaciens*" Nature Biotechnology 14:745-750 (1996). The virulence functions of the *Agrobacterium tumefaciens* host will direct the insertion of the construct into the plant cell DNA when the cell is infected by the bacteria. See, for example Horsch et al., Science 233: 496-498 (1984), and Fraley et al., Proc. Natl. Acad. Sci. 80: 4803 (1983). Viral replication systems using a virus or viral nucleic acids and using viral DNA and RNA molecules are known. See, for example, U.S. Pat. Nos. 6,660,500, 6,462,255, 5,889,190 and 5,889,101.

Standard methods for transformation of canola are described at Moloney et al. "High Efficiency Transformation of *Brassica napus* using *Agrobacterium* Vectors" Plant Cell Reports 8:238-242 (1989). Corn transformation is described by Fromm et al, Bio/Technology 8:833 (1990) and Gordon-Kamm et al, supra. *Agrobacterium* is primarily used in dicots, but certain monocots can be transformed by *Agrobacterium*. See supra and U.S. Pat. No. 5,550,318. Rice transformation is described by Hiei et al., "Efficient Transformation of Rice (*Oryza sativa* L.) Mediated by *Agrobacterium* and Sequence Analysis of the Boundaries of the T-DNA" The Plant Journal 6(2): 271-282 (1994, Christou et al, Trends in Biotechnology 10:239 (1992) and Lee et al, Proc. Nat'l Acad. Sci. USA 88:6389 (1991). Wheat can be transformed by techniques similar to those used for transforming corn or rice. *Sorghum* transformation is described at Casas et al, supra and sorghum by Wan et al, Plant Physiol. 104:37 (1994). Soybean transformation is described in a number of publications, including U.S. Pat. No. 5,015,580. Cotton transformation is described at U.S. Pat. No. 5,004,863; US patent Number; Christou, (1992) Plant Journal Vol. 2 (3) 275-281 Kumar et al. (2004) Plant Mol. Biol. 56, 203-216.

In one preferred method, use of aerosol beam technology for introduction of nucleotide sequences into cells is employed. Aerosol beam technology employs the jet expansion of an inert gas as it passes from a region of higher gas pressure to a region of lower gas pressure through a small orifice. The expanding gas accelerates aerosol droplets containing the molecules to be introduced into a cell or tissue. DNA carried in aerosol droplets of this small size penetrates cells only because of the speeds attained by the aerosol droplets. Speeds achieved by the aerosol beam method of the invention are supersonic and can reach 2,000 meters/second. In a preferred embodiment, the process includes (I) culturing a source of cells, (II) optionally, pretreating cells to yield tissue with increased capacity for uptake and integration by aerosol beam technology, (III) transforming said tissue with an exogenous nucleotide sequence by the aerosol beam method of the invention, (IV) optionally, identifying or selecting for transformed tissue, (V) optionally regenerating transgenic plants from the transformed cells or tissue, and (VI) optionally, producing progeny of said transgenic plants. This process is described in detail at Held et al., U.S. Pat. Nos. 6,809,232; 7,067,716; and 7,026,286.

The following is provided by way of illustration and not intended to limit the scope of the invention.

EXAMPLE 1

Optimized 2mEPSPS v2 Encoding Nucleotide Sequence

Analysis of the DNA sequence of the 2mEPSPS v1 from *Zea mays* coding region revealed the presence of several sequence motifs that were believed to be detrimental to optimal plant expression, as well as a non-optimal codon composition for expression in dicotyledonous plants. Thus, an achievement of the present invention is design of plant optimized gene encoding a 2mEPSPS v2 to generate a DNA sequence that can be expressed optimally in both dicotyledonous and monocotyledonous plants, and in which the sequence modifications do not hinder translation or create mRNA instability.

Due to the plasticity afforded by the redundancy/degeneracy of the genetic code (i.e., some amino acids are specified by more than one codon), evolution of the genomes in different organisms or classes of organisms has resulted in differential usage of synonymous codons. This "codon bias" is reflected in the mean base composition of protein coding regions. For example, organisms having genomes with relatively low G+C contents utilize more codons having A or T in the third position of synonymous codons, whereas those having higher G+C contents utilize more codons having G or C in the third position. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons would have correspondingly low translation rates. This rate could be reflected by correspondingly low levels of the encoded protein.

In engineering a gene encoding 2mEPSPS for expression in dicotyledonous plants (such as cotton, canola, tobacco) and particularly soybean as well as monocotyledonous plants (such as rice, maize, or wheat), it is helpful if the codon bias of the prospective host plant(s) has been determined. Multiple publicly available DNA sequence databases exist wherein one may find information about the codon distribution of plant genomes or the protein coding regions of various plant genes. The codon bias is the statistical distribution of codons that the plant uses for coding the amino acids of its proteins. The preferred codon usages for dicots and monocots (maize) are shown in Table 1.

preferred, etc.) codons to specify the amino acid at each position within the amino acid sequence. The new sequence is then analyzed for restriction enzyme sites that might have been created by the modifications. The identified sites are further modified by replacing the codons with first, second, third, or fourth choice preferred codons. Other sites in the sequence which could affect transcription or translation of the gene of interest are the stem loop structures, exon:intron junctions (5' or 3'), poly A addition signals, or RNA polymerase termination signals; these sites are removed by the substitution of plant codons. The sequence is further analyzed and modified to reduce the frequency of TA or GC doublets. In addition to the doublets, G or C sequence blocks that have more than about six residues that are the same can affect transcription or translation of the sequence. Therefore, these

TABLE 1

Synonymous codon representation from coding regions of monocotyledonous (maize %) and dicotyledonous (dicot %) plant genes are shown in Columns D, E, I, and J. Values for a balanced-biased codon representation set for a plant-optimized synthetic gene design are in Columns C and H.

| A<br>Amino<br>Acid | B<br>Codon | C<br>Weighted<br>Average | D<br>Maize<br>% | E<br>Dicot<br>% | F<br>Amino<br>Acid | G<br>Codon | H<br>Weighted<br>Average | I<br>Maize<br>% | J<br>Dicot<br>% |
|---|---|---|---|---|---|---|---|---|---|
| ALA (A) | GCA | 25.5 | 18 | 25 | LEU (L) | CTA | DNU | 8 | 8 |
| 100 | GCC | 35.6 | 34 | 27 | 100 | CTC | 34.3 | 26 | 19 |
|  | GCG | DNU | 24 | 6 |  | CTG | DNU | 29 | 9 |
|  | GCT | 39.0 | 24 | 42 |  | CTT | 34.3 | 17 | 28 |
| ARG (R) | AGA | 27.4 | 15 | 30 |  | TTA | DNU | 5 | 10 |
| 100 | AGG | 31.5 | 26 | 25 |  | TTG | 31.4 | 15 | 26 |
|  | CGA | DNU | 9 | 8 | LYS (K) | AAA | 30.6 | 22 | 39 |
|  | CGC | 21.7 | 24 | 11 | 100 | AAG | 69.4 | 78 | 61 |
|  | CGG | DNU | 15 | 4 | MET (M) | ATG | 100 | 100 | 100 |
|  | CGT | 19.4 | 11 | 21 | PHE (F) | TTC | 63.2 | 71 | 55 |
| ASN (N) | AAC | 61.4 | 68 | 55 | 100 | TTT | 36.8 | 29 | 45 |
| 100 | AAT | 38.6 | 32 | 45 | PRO (P) | CCA | 41.4 | 26 | 42 |
| ASP (D) | GAC | 52.6 | 63 | 42 | 100 | CCC | 25.3 | 24 | 17 |
| 100 | GAT | 47.4 | 37 | 58 |  | CCG | DNU | 28 | 9 |
| CYC C | TGC | 61.8 | 68 | 56 |  | CCT | 33.3 | 22 | 32 |
| 100 | TGT | 38.2 | 32 | 44 | SER (S) | AGC | 26.0 | 23 | 18 |
| END | TAA |  | 20 | 48 | 100 | AGT | DNU | 9 | 14 |
| 100 | TAG |  | 21 | 19 |  | TCA | 22.4 | 16 | 19 |
|  | TGA |  | 57 | 33 |  | TCC | 26.3 | 23 | 18 |
| GLN (Q) | CAA | 48.4 | 38 | 59 |  | TCG | DNU | 14 | 6 |
| 100 | CAG | 51.6 | 62 | 41 |  | TCT | 25.4 | 15 | 25 |
| GLU (E) | GAA | 38.8 | 29 | 49 | THR (T) | ACA | 28.0 | 21 | 27 |
| 100 | GAG | 61.2 | 71 | 51 | 100 | ACC | 39.5 | 37 | 30 |
| GLY (G) | GGA | 28.5 | 19 | 38 |  | ACG | DNU | 22 | 8 |
| 100 | GGC | 29.0 | 42 | 16 |  | ACT | 32.5 | 20 | 35 |
|  | GGG | 16.0 | 20 | 12 | TRP (W) | TGG | 100 | 100 | 100 |
|  | GGT | 26.6 | 20 | 33 | TYR (Y) | TAC | 65.0 | 73 | 57 |
| HIS (H) | CAC | 54.1 | 62 | 46 | 100 | TAT | 35.0 | 27 | 43 |
| 100 | CAT | 45.9 | 38 | 54 | VAL (V) | GTA | DNU | 8 | 12 |
| ILE (I) | ATA | 15.9 | 14 | 18 | 100 | GTC | 28.7 | 32 | 20 |
| 100 | ATC | 47.9 | 58 | 37 |  | GTG | 38.0 | 39 | 29 |
|  | ATT | 36.4 | 28 | 45 |  | GTT | 33.3 | 21 | 39 |

*DNU = Do Not Use

The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons). In designing coding regions for plant expression of, the primary ("first choice") codons preferred by the plant should be determined, as well as the second, third, fourth etc. choices of preferred codons when multiple choices exist. A new DNA sequence can then be designed which encodes the amino acid sequence of the same 2mEPSPS peptide, but the new DNA sequence differs from the original DNA sequence by the substitution of plant (first preferred, second preferred, third preferred, or fourth blocks are advantageously modified by replacing the codons of first or second choice, etc. with the next preferred codon of choice.

One may thus use a variety of methods to produce a gene as described herein. An example of one such approach is further illustrated in PCT App. WO 97/13402. Thus, synthetic genes which express a functional 2mEPSPS protein, can be used to transform hosts, including plants. Additional guidance regarding the production of synthetic genes can be found in, for example, U.S. Pat. No. 5,380,831.

To engineer a plant-optimized gene encoding a 2mEPSPS v2, a DNA sequence was designed to encode the amino acid sequences utilizing a redundant genetic code established from a codon bias table compiled from the protein coding sequences for the particular host plants. In Table 1, Columns D, E, I and J present the distributions (in % of usage for all codons for that amino acid) of synonymous codons for each amino acid, as found in the coding regions of monocotyledonous (maize) and dicotyledonous plants. Some synonymous codons for some amino acids are found only rarely in plant genes (e.g. CGG). Usually, a codon was considered to be rarely used if it is represented at about 10% or less of the time to encode the relevant amino acid in genes of either plant type (indicated by DNU in Columns C and H of Table 1). To balance the distribution of the remaining codon choices for an amino acid, a Weighted Average representation for each codon was calculated, using the formula:

Weighted Average % of $C1 = 1/(\% C1 + \% C2 + \% C3 + etc.) \times \% C1 \times 100$ where C1 is the codon in question and % C2, % C3, etc. represent the averages of the % values for soybean of remaining synonymous codons (average % values for the relevant codons are taken from Columns C and G) of Table 1.

The Weighted Average % value for each codon is given in Columns C and H of Table 1.

A new DNA sequence which encodes essentially the amino acid sequence of the 2mEPSPS protein was designed for optimal expression in dicotyledonous plants and particularly soybean, as well as monocotyledonous plants, using a balanced codon distribution of frequently used codons found in monocotyledonous and dicotyledonous plant genes. The new DNA sequences differ from the original DNA sequences by the substitution of plant (first preferred, second preferred, third preferred, or fourth preferred) codons to specify the appropriate amino acid at each position within the protein amino acid sequence. Design of the plant-optimized DNA sequences were initiated by reverse-translation of the protein sequences of the *Zea mays* 2mEPSPS protein sequence (SEQ ID NO: 3) using a monocot/dicot codon bias table constructed from Table 1 Columns C and H. The initial sequences were then modified by compensating codon changes (while retaining overall weighted average codon representation) to remove or add restriction enzyme recognition sites, remove highly stable intrastrand secondary structures, and remove other sequences that might be detrimental to cloning manipulations or expression of the engineered gene in plants. The DNA sequences were then re-analyzed for restriction enzyme recognition sites that might have been created by the modifications. The identified sites were further modified by replacing the relevant codons with first, second, third, or fourth choice preferred codons. Other sites in the sequences that could affect transcription or translation of the gene of interest include the exon:intron junctions (5' or 3'), poly A addition signals, or RNA polymerase termination signals. The modified sequences were further analyzed and further modified to reduce the frequency of TA or CG doublets, and to increase the frequency of TG or CT doublets. In addition to these doublets, sequence blocks that have more than about six consecutive residues of [G+C] or [A+T] can affect transcription or translation of the sequence. Therefore, these sequence blocks were also modified by replacing the codons of first or second choice, etc. with other preferred codons of choice. Rarely used codons are not included to a substantial extent in the gene design, being used only when necessary to accommodate a different design criterion than codon composition per se (e.g. addition or deletion of restriction enzyme recognition sites).

The newly designed, monocotyledonous and dicotyledonous plant optimized 2mEPSPS v2 DNA sequence is listed in SEQ ID NO: 5 shown in FIG. 3 (full-length sequence including "atg" start codon is disclosed as SEQ ID NO: 7). The resulting DNA sequence has a higher degree of codon diversity, a desirable base composition, contains strategically placed restriction enzyme recognition sites, and lacks sequences that might interfere with transcription of the gene, or translation of the product mRNA. Table 2 presents a comparison of the codon compositions of the coding regions for the 2mEPSP protein as found in the original gene and the monocotyledonous and dicotyledonous plants-optimized version, and compares both to the codon composition recommendations for a monocotyledonous and dicotyledonous plants optimized sequence as calculated from Table 1 Columns C and H.

TABLE 2

Values for a balanced-biased codon representation set for a plant-optimized synthetic gene design. DNU = Do Not Use

| Amino Acid | Codon | Reco m'd Gene # | Gene # | Gene % | Weighted Average | Maize % | Dicot % |
|---|---|---|---|---|---|---|---|
| ALA (A) | GCA | 12 | 12 | 26.1 | 25.5 | 18 | 25 |
| 46 | GCC | 16 | 16 | 34.8 | 35.6 | 34 | 27 |
| | GCG | 0 | 0 | 0.0 | DNU | 24 | 6 |
| | GCT | 18 | 18 | 39.1 | 39.0 | 24 | 42 |
| ARG (R) | AGA | 5 | 6 | 30.0 | 27.4 | 15 | 30 |
| 20 | AGG | 6 | 6 | 30.0 | 31.5 | 26 | 25 |
| | CGA | 20 | 0 | 0.0 | DNU | 9 | 8 |
| | CGC | 4 | 4 | 20.0 | 21.7 | 24 | 11 |
| | CGG | 0 | 0 | 0.0 | DNU | 15 | 4 |
| | CGT | 4 | 4 | 20.0 | 19.4 | 11 | 21 |
| ASN (N) | AAC | 7 | 7 | 63.6 | 61.4 | 68 | 55 |
| 11 | AAT | 4 | 4 | 36.4 | 38.6 | 32 | 45 |
| ASP (D) | GAC | 14 | 13 | 50.0 | 42.6 | 63 | 42 |
| 26 | GAT | 12 | 13 | 50.0 | 47.4 | 37 | 58 |
| CYS (C) | TGC | 4 | 3 | 42.9 | 61.8 | 68 | 56 |
| 7 | TGT | 3 | 4 | 57.1 | 38.2 | 32 | 44 |

TABLE 2-continued

Values for a balanced-biased codon representation set for a plant-optimized synthetic gene design. DNU = Do Not Use

| Amino Acid | Codon | Reco m'd Gene # | Gene # | Gene % | Weighted Average | Maize % | Dicot % |
|---|---|---|---|---|---|---|---|
| END 1 | TAA | | 0 | 0.0 | | 20 | 48 |
| | TAG | | 0 | 0.0 | | 21 | 19 |
| | TGA | | 1 | 100.0 | | 59 | 33 |
| GLN (Q) | CAA | 3 | 3 | 50.0 | 48.4 | 38 | 59 |
| 6 | CAG | 3 | 3 | 50.0 | 51.6 | 62 | 41 |
| GLU (E) | GAA | 11 | 11 | 39.3 | 38.8 | 29 | 38 |
| 28 | GAG | 17 | 17 | 60.7 | 31.2 | 71 | 16 |
| GLY (G) | GGA | 12 | 13 | 31.0 | 28.5 | 19 | 12 |
| 42 | GGC | 12 | 11 | 26.2 | 29.0 | 42 | 16 |
| | GGG | 7 | 7 | 16.7 | 16.0 | 20 | 12 |
| | GGT | 11 | 11 | 26.2 | 26.6 | 20 | 33 |
| HIS (H) | CAC | 2 | 2 | 50.0 | 54.1 | 62 | 46 |
| 4 | CAT | 2 | 2 | 50.0 | 45.9 | 38 | 54 |
| ILE (I) | ATA | 3 | 3 | 13.6 | 15.9 | 14 | 18 |
| 22 | ATC | 11 | 11 | 50.0 | 47.9 | 58 | 37 |
| | ATT | 8 | 8 | 36.4 | 36.4 | 28 | 45 |
| LEU (L) | CTA | 0 | 0 | 0.0 | DNU | 8 | 8 |
| 42 | CTC | 14 | 14 | 33.3 | 34.3 | 26 | 19 |
| | CTG | 0 | 0 | 0.0 | DNU | 29 | 9 |
| | CTT | 14 | 14 | 33.3 | 34.3 | 17 | 28 |
| | TTA | 0 | 0 | 0.0 | DNU | 5 | 10 |
| | TTG | 13 | 14 | 33.3 | 31.4 | 15 | 26 |
| LYS (K) | AAA | 8 | 8 | 30.8 | 30.6 | 22 | 39 |
| 26 | AAG | 18 | 18 | 69.2 | 69.4 | 78 | 61 |
| MET (M) | ATG | 15 | 15 | 100 | 100 | 100 | 100 |
| PHE (F) | TTC | 8 | 8 | 61.5 | 63.2 | 71 | 55 |
| 13 | TTT | 5 | 5 | 38.5 | 36.8 | 29 | 45 |
| PRO (P) | CCA | 9 | 9 | 40.9 | 41.4 | 26 | 42 |
| | CCC | 6 | 6 | 27.3 | 25.3 | 24 | 17 |
| | CCG | 0 | 0 | 0.0 | DNU | 28 | 9 |
| | CCT | 7 | 7 | 31.8 | 33.3 | 22 | 32 |
| SER (S) | AGC | 7 | 7 | 26.9 | 26.0 | 23 | 18 |
| 26 | AGT | 0 | 0 | 0.0 | DNU | 9 | 14 |
| | TCA | 6 | 6 | 23.1 | 22.4 | 16 | 19 |
| | TCC | 7 | 7 | 26.9 | 26.3 | 23 | 18 |
| | TCG | 0 | 0 | 0.0 | DNU | 14 | 6 |
| | TCT | 7 | 6 | 23.1 | 25.4 | 15 | 25 |
| THR (T) | ACA | 9 | 9 | 29.0 | 28.0 | 21 | 27 |
| 31 | ACC | 12 | 12 | 38.7 | 39.5 | 37 | 30 |
| | ACG | 0 | 0 | 0.0 | DNU | 22 | 8 |
| | ACT | 10 | 10 | 32.3 | 32.5 | 20 | 35 |
| TRP (W) | TGG | 3 | 3 | 100 | 100 | 100 | 100 |
| TYR (Y) | TAC | 7 | 7 | 63.6 | 65.0 | 73 | 57 |
| 11 | TAT | 4 | 4 | 36.4 | 35.0 | 27 | 43 |
| VAL (V) | GTA | 0 | 0 | 0.0 | DNU | 8 | 12 |
| 44 | GTC | 13 | 13 | 29.5 | 28.7 | 32 | 20 |
| | GTG | 17 | 17 | 38.6 | 38.0 | 39 | 29 |
| | GTT | 15 | 14 | 31.8 | 33.3 | 21 | 39 |

Once a plant-optimized DNA sequence has been designed on paper or in silico, actual DNA molecules can be synthesized in the laboratory to correspond in sequence precisely to the designed sequence. Such synthetic DNA molecules can be cloned and otherwise manipulated exactly as if they were derived from natural or native sources. Synthesis of DNA fragments comprising SEQ ID NOS 5 and 7 containing additional sequences such as 6-frame stops (stop codons located in all six reading frames which are added to the 3' end of the coding sequence) and a 5' NcoI restriction site for cloning were performed by commercial suppliers (DNA2.0, Menlo Park, Calif.). The synthetic DNA was then cloned into expression vectors and transformed into soybean as described in the Examples below.

EXAMPLE 2

Preparation of Plasmids

Construction of pDAB8290

A codon optimized version of the 2mEPSPS coding sequence was synthesized and labeled as 2mEPSPS v2. This coding sequence was cloned into pDAB8261 as a Bgl II—Spe I fragment. The resulting 2mEPSPS v2 expression cassette construct consisted of the following gene elements; Histone H4A748 Promoter::Histone Intron 2::Optimized Transit Peptide (OTPc)::2mEPSPS v2::Histone H4A748 3'UTR Terminator.

Plasmids containing the 2mEPSPS v2 expression cassette were identified via restriction enzyme and DNA sequencing analysis. The resulting plasmid was labeled as pDAB8290.

Construction of pDAB8291

The construct containing the Histone H4A748 Promoter::Histone Intron 2::Optimized Transit Peptide::2mEPSPS v2 Histone H4A748 3'UTR Terminator was liberated from pDAB8290 as an Asc I fragment and cloned into a corresponding Asc I enzyme site of pDAB4468 which contains the pat (supra) and AAD-12 expression cassette (WO 2007/053482 A2). Plasmids containing the 2mEPSPS v2 expression cassette cloned in the trans 2mEPSPS v2 orientation (← → →) to the aad-12 and pat expression cassettes were identified via restriction enzyme and DNA sequencing analysis. The resulting binary plasmid was labeled as pDAB8291 (FIG. 5)

Histone H4A748 refers to the promoter from the histone 4 gene (see, Chaboute et al. Plant Molecular Biology, 8:179-191 (1987)). The histone intron is the first intron of gene II of the histone H3.III variant of *Arabidopsis thaliana*. Chaubet et al. Journal of Molecular Biology, 225:569-574 (1992). OTPc refers to the optimized transit peptide. See, U.S. Pat. No. 5,510,471. Histone H4A748 3' UTR refers to the terminator from H4A748 as described at Chaboute et al. (1987) supra. AtUbi10 refers to the *Arabidopsis thaliana* Ubiquitin 10 promoter (see, Callis, et al., (1990) *J. Biol. Chem.*, 265: 12486-12493). The reference of aad-12 describes a gene encoding an enzyme capable of degrading 2,4-D and pyridyloxy acetate herbicides (WO 2007/053482 A2). AtuORF23 3'UTR refers to the Open Reading Frame 23 3' Untranslated Region from *Agrobacterium tumefaciens* (see, U.S. Pat. No. 5,428,147) The CsVMV promoter refers to the cassaya vein mosaic virus promoter described at Verdauger et al. Plant Mol. Biol. 31:1129-1139 (1996). *Plant Science* Vol. 169, Issue 4, pp. 704-711 (2005). The annotation of pat refers to a gene encoding phosphinothricin acetyl transferase capable of degrading phosphinothricin (see, Wohlleben et al., (1988) *Gene* 70: 25-37). AtuORF1 3'UTR refers to the Open Reading Frame 1 3' Untranslated Region from *Agrobacterium tumefaciens* (see, Huang et al., (1990) *J. Bacteriol.* 172:1814-1822). RB7 MAR refers to the RB7 matrix attachment region, as described at Thompson and Myatt, (1997) *Plant Mol. Biol.*, 34: 687-692 and WO9727207.

A deposit of 2500 seeds having the two events produced containing the nucleotide sequence of the invention is deposited with the ATCC deposit number PTA-11335 and PTA-11337 with the American Type Culture Collection (ATCC), 10801 University Boulevard, Manassas, Va. 20110-2209 USA. The seeds were deposited with the ATCC on Sep. 14, 2010. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent

EXAMPLE 3

Plant Transformation

Transgenic soybean (*Glycine max*) was generated through *Agrobacterium*-mediated transformation of soybean cotyledonary node explants. The disarmed *Agrobacterium* strain EHA101 (Hood E., Helmer G., Fraley R., Chilton M., (1986) *J. Bacteriol.*, 168: 1291-1301) carrying the binary vector pDAB8291 containing the selectable marker, pat, and the genes of interest, aad-12 and 2mEPSPS v2, within the T-strand DNA region, was used to initiate transformation.

*Agrobacterium*-mediated transformation was carried out using a modified procedure of Zeng et al. (Zeng P., Vadnais D. A., Zhang Z., Polacco J. C., (2004), *Plant Cell Rep.*, 22(7): 478-482). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were treated topically (leaf paint technique) with glufosinate to screen for putative transformants. The screened plantlets were transferred to the greenhouse, allowed to acclimate and then leaf-painted with glufosinate to reconfirm tolerance. These putative transformed $T_0$ plants were sampled and molecular analyses was used to confirm the presence of pat, aad-12 and 2mEPSPS v2. $T_0$ plants were allowed to self fertilize in the greenhouse to give rise to $T_1$ seed.

EXAMPLE 4

Molecular Confirmation

Flanking genomic DNA border regions of soybean events were isolated and determined to confirm the presence of the T-strand insertion into a chromosomal genomic location site. Genomic sequence was confirmed for the 5' flanking border sequence and 3' flanking border sequence. PCR amplification based on these border sequences was used to validate that the border regions were of soybean origin and that the junction regions contained an introgressed T-strand from pDAB8291. Overall, the characterization of the insert and border sequence for the soybean events indicated that an intact copy of the T-strand was present in the soybean genome.

Southern blot analysis was also used to establish the integration pattern of pDAB8291 into the soybean genome. The Southern blot data suggested that a T-strand fragment inserted into the genome of the isolated soybean events. Detailed Southern blot analysis was conducted using gene-specific probes to aad-12 and 2mEPSPS v2 gene, contained in the T-strand integration region of pDAB8291. Descriptive restriction enzymes that have cleavage sites located within the plasmid and produce hybridizing fragments internal to the plasmid or fragments that span the junction of the plasmid with soybean genomic DNA (border fragments) were generated and hybridized with the probes described above. The molecular weights from the Southern hybridization for the combination of the restriction enzyme and the probe were unique for each event. These experiments demonstrated that the aad-12, pat, and 2mEPSPS v2 transgenes integrated within the soybean genome without rearrangement. Soybean events were characterized as full length, simple insertion events containing the aad-12, pat and 2mEPSPS v2 plant transformation unit (PTU) from plasmid pDAB8291.

EXAMPLe 5

Protein Expression of 2mEPSPS in Planta

Levels of 2mEPSPS were determined to be present in soybean events transformed with pDAB8291 at the $T_5$ generation. The soluble, extractable 2mEPSPS protein from soybean leaf tissue was measured using a Western blot method.

Figure 6:
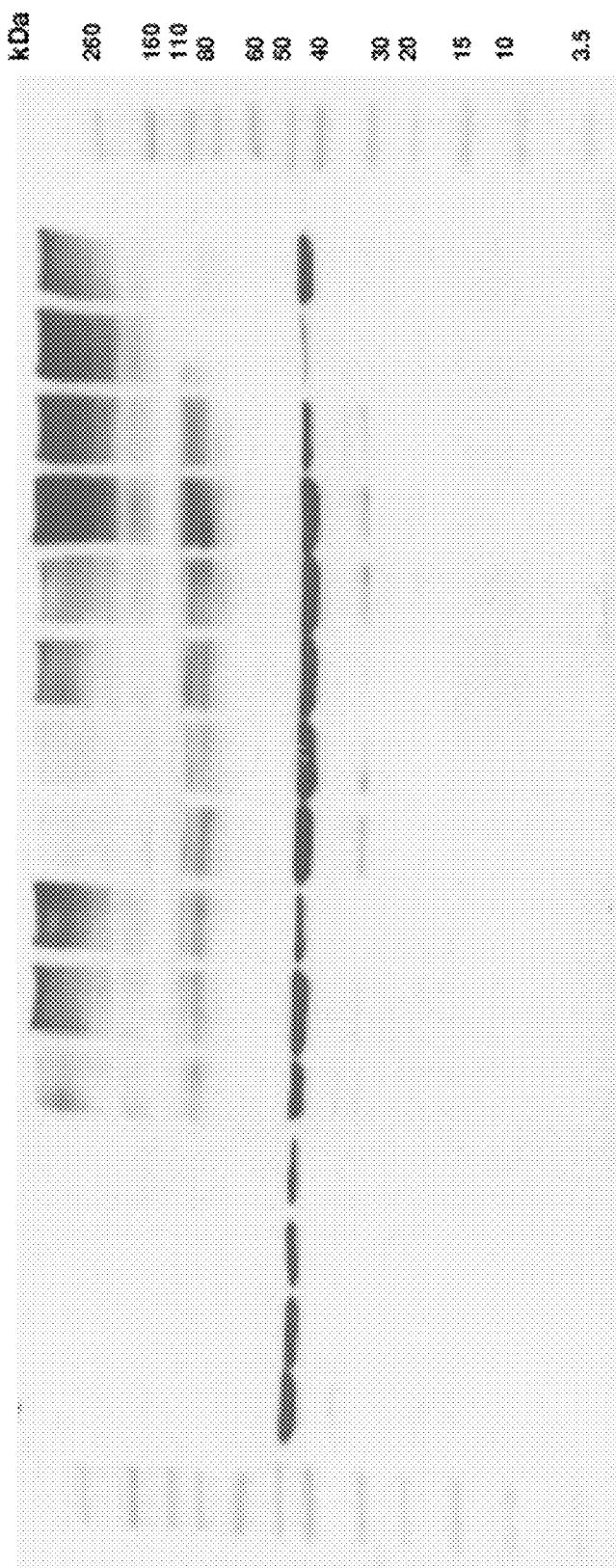
FIG. 6 is a Western blot of a first event expressing 2mEPSPS v2.
Figure 7:
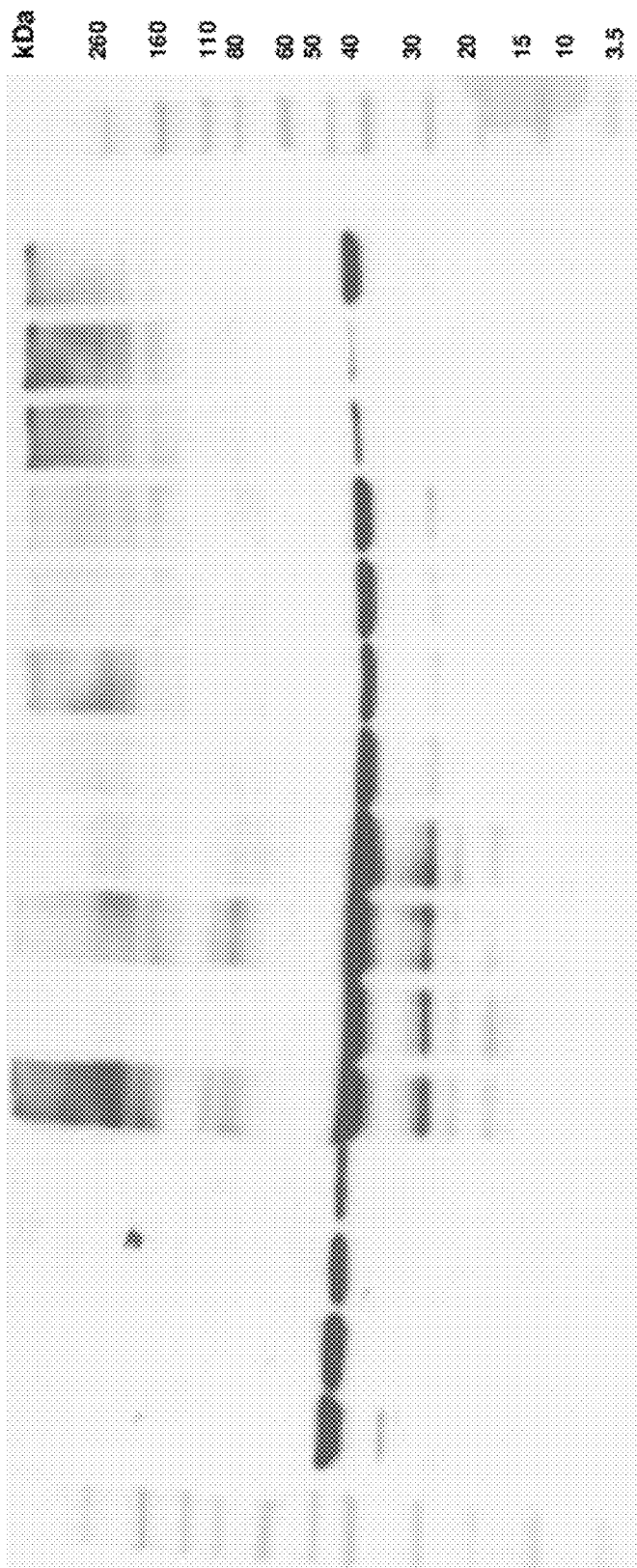
FIG. 7 is a Western blot of a second event expressing 2mEPSPS v2.

Sprayed and unsprayed plants were sampled at the $R_3$ stage of development. Spray treatments consisted of a tank mix of 2,240 g ae/ha glyphosate and 2,240 g ae/ha 2,4-D applied at the $V_6/V_7$ stage of development. 2mEPSPS was extracted from soybean plant tissues with a phosphate buffered saline solution containing the detergent Tween-20 (PBST) and 0.5% Bovine Serum Albumin (BSA). The plant tissue was centrifuged; the aqueous supernatant was collected and diluted with appropriate buffer as necessary. The proteins were separated using SDS-PAGE gel and transferred to a nylon membrane. The resultant Western blots were probed with antibodies specific for the 2mEPSPS mutant as described at U.S. Pat. No. 7,807,791, incorporated herein by reference in its entirety, to investigate stability of 2mEPSPS from pDAB8291 events. The Western blots of the two events are shown in FIGS. 6 and 7. Lanes 1 and 18 are molecular markers; lanes 2-5 show the 2mEPSPS protein standard at 2, 1, 0.5 and 0.25 ng/well. Lanes 6-9 are unsprayed soybean events with the optimized 2mEPSPS v2. Lanes 10-13 are sprayed soybean events with optimized 2mEPSPS v2. The spray treatment consisted of a tank mix of 2,240 g ae/ha glyphosate and 2,240 g ae/ha 2,4-D. Lanes 14-16 are unsprayed soybean events with non-optimized 2mEPSPS and lane 17 is the non-transgenic variety "Maverick."

Soybean events expressing 2mEPSPS were stable and for each event with little to no protein truncation or evidence of degradation. No significant differences in expression were observed between sprayed and un-sprayed soybean events.

The molecular weight of the protein isolated from the soybean events expressing 2mEPSPS was the same for the protein standard and positive control, which contained an unoptimized 2mEPSPS. Finally, the band intensity of the protein samples purified from the soybean events was more intense than a positive control soybean plant, containing an unoptimized 2mEPSPS. The Western blot data indicated robust expression of full-length 2mEPSPS.

EXAMPLE 5

In Planta Tolerance to Glyphosate Provided by 2mEPSPS

Soybean events containing the 2mEPSPv2 expression cassette construct from pDAB8291 are tolerant to glyphosate. Field trials were performed during the 2009 and 2010 growing seasons. The plots were planted with the transgenic soybean seed which had been produced from the transformation with pDAB8291 and non-transgenic soybean (cv Maverick) which was used as a control. Field grown soybean plants from the $T_2$ and $T_4$ generation were sprayed with high rates of glyphosate. Glyphosate (DURANGO® herbicide Dow AgroSciences, Indianapolis, Ind.) applications were made at the $V_3$ or $V_5$ stage of plant development at a rate of 2,240 g ae/ha. Seven days after glyphosate application, the plants were assessed for injury. Minimal damage to the soybean plants transformed with pDAB8291 was observed as compared to Maverick controls (Table 3).

TABLE 3

Tolerance of Soybean Events expressing 2mEPSPS (construct pDAB8291) to 2,240 g ae/ha Glyphosate.

| Event Name | Generation | Application Growth Stage | Adjusted Mean Injury 7daa(%) |
|---|---|---|---|
| 8291-4524 | $T_2$ | $V_3$ | 10 |
| 8291-4536 | $T_2$ | $V_3$ | 3.5 |
| Maverick | $T_2$ | $V_3$ | 100 |
| 8291-4524 | $T_4$ | $V_5$ | 0.5 |
| 8291-4536 | $T_4$ | $V_5$ | 0.75 |
| Maverick | $T_4$ | $V_5$ | 100 |

Thus, the optimized version of 2mEPSPS v2 provides resistance to glyphosate when expressed in plants.

What is claimed is:

1. A nucleic acid molecule encoding a 5-enolpyruvyl-3-phosphoshikimic acid synthase (EPSPS) comprising a nucleic acid sequence selected from the group consisting of:
   a) SEQ ID NO: 5; and
   b) a nucleic acid molecule comprising the complete compliment of SEQ ID NO: 5.

2. A nucleic acid molecule encoding a 5-enolpyruvyl-3-phosphoshikimic acid synthase (EPSPS) comprising SEQ ID NO: 5.

3. A construct comprising a nucleic acid sequence selected from the group consisting of:
   a) SEQ ID NO: 5; and
   b) a nucleic acid molecule comprising the complete compliment of SEQ ID NO: 5.

4. A vector comprising at least one construct of claim 3.

5. A plant cell comprising a nucleic acid sequence selected from the group consisting of:
   a) SEQ ID NO: 5; and
   b) a nucleic acid molecule comprising the complete compliment of SEQ ID NO: 5.

6. The plant cell of claim 5 wherein said plant cell is a soybean plant cell.

7. A plant comprising a nucleic acid sequence selected from the group consisting of:
   a) SEQ ID NO: 5; and
   b) a nucleic acid molecule comprising the complete compliment of SEQ ID NO: 5.

8. The plant of claim 7, wherein said plant is a soybean plant.

9. The plant of claim 7, wherein said plant is resistant to glyphosate herbicide as a result of expression of said nucleic acid molecule.

10. The plant of claim 9, further comprising a second nucleic acid molecule encoding a polypeptide that provides resistance to a second herbicide.

11. A method of producing a plant having increased resistance to exposure to a phosphonomethylglycine herbicide, said method comprising,
   a) introducing into said plant a nucleic acid molecule encoding a 5-enolpyruvyl-3-phosphoshikimic acid synthase (EPSPS) comprising a nucleic acid sequence selected from the group consisting of:
      i. SEQ ID NO: 5; and
      ii. a nucleic acid molecule comprising the complete compliment of SEQ ID NO: 5;
      v. and
   b) producing a plant having increased resistance to exposure to a phosphonomethylglycine herbicide than a plant not comprising said nucleic acid molecule.

12. The method of claim 11, wherein said plant is a soybean plant.

13. A method for selectively inhibiting growth of plants, said method comprising,
   a) planting seeds, at least one of said seeds comprising a nucleic acid molecule encoding a 5-enolpyruvyl-3-phosphoshikimic acid synthase (EPSPS) comprising a nucleic acid sequence selected from the group consisting of:
      i. SEQ ID NO: 5; and
      ii. a nucleic acid molecule comprising the complete compliment of SEQ ID NO: 5,
      v. and
   b) growing plants from said seeds, exposing said seeds or plants to glyphosate herbicide such that growth of any of said plants or seeds not comprising said nucleic acid molecule is inhibited.

14. A method of selecting for a transformed plant cell, said method comprising,
   a) transforming a population of plant cells with a nucleic acid molecule comprising a nucleic acid sequence selected from the group consisting of:
      i. SEQ ID NO: 5; and
      ii. a nucleic acid molecule comprising the complete compliment of SEQ ID NO: 5
      v. and
   b) exposing said population of plant cells to a glyphosate herbicide such that growth of plant cells not comprising said nucleic acid molecule is inhibited.

15. A method of detecting if a plant comprises a nucleic acid sequence conferring increased resistance to a glyphosate herbicide, said method comprising collecting a sample from said plant and assaying said sample for presence of a nucleic acid sequence selected from the group consisting of:

a) SEQ ID NO: 5; and
b) a nucleic acid molecule comprising the complete compliment of SEQ ID NO: 5.

16. The plant cell of claim 5, said plant cell further comprising at least one second nucleic acid molecule encoding a polypeptide conferring increased resistance to a herbicide selected from the group consisting of α-ketoglutarate-dependent dioxygenase (AAD-12), hydroxyphenylpyruvate dioxygenase (HPPD), acetolactase synthase (ALS), protoporphyrinogen oxidase (PPO), dicamba, glufosinate, phosphinothricin, bialaphos and which binds to core proteins of photosystem II reaction centers (PSII) compared to a plant not comprising said at least one second nucleic acid molecule.

17. The plant cell of claim 16, said plant cell further comprising at least one third nucleic acid molecule encoding a polypeptide conferring increased resistance to a herbicide selected from the group consisting of α-ketoglutarate-dependent dioxygenase (AAD-12), hydroxyphenylpyruvate dioxygenase (HPPD), acetolactase synthase (ALS) enzyme, protoporphyrinogen oxidase (PPO), dicamba, glufosinate, phosphinothricin, bialaphos and which binds to core proteins of photosystem II reaction centers (PSII) compared to a plant not comprising said at least one second nucleic acid molecule.

18. The method of claim 11, further comprising introducing into said plant at least one second nucleic acid molecule encoding a polypeptide conferring increased resistance to a herbicide selected from the group consisting of α-ketoglutarate-dependent dioxygenase (AAD-12), hydroxyphenylpyruvate dioxygenase (HPPD), acetolactase synthase (ALS) enzyme, protoporphyrinogen oxidase (PPO), dicamba, glufosinate, phosphinothricin, bialaphos and which binds to core proteins of photosystem II reaction centers (PSII) compared to a plant not comprising said at least one second nucleic acid molecule.

19. The method of claim 18, further comprising introducing into said plant at least one third nucleic acid molecule encoding a polypeptide conferring increased resistance to a herbicide selected from the group consisting of α-ketoglutarate-dependent dioxygenase (AAD-12), hydroxyphenylpyruvate dioxygenase (HPPD), acetolactase synthase (ALS) enzyme, protoporphyrinogen oxidase (PPO), dicamba, glufosinate, phosphinothricin, bialaphos and which bind to core proteins of photosystem II reaction centers (PSII) compared to a plant not comprising said at least one second nucleic acid molecule.

20. The method of claim 13, wherein at least one of said seeds comprising said nucleic acid molecule further comprises at least one second nucleic acid molecule encoding a polypeptide conferring increased resistance to a herbicide selected from the group consisting of α-ketoglutarate-dependent dioxygenase (AAD-12), hydroxyphenylpyruvate dioxygenase (HPPD), acetolactase synthase (ALS) enzyme, protoporphyrinogen oxidase (PPO), dicamba, glufosinate, phosphinothricin, bialaphos and which binds to core proteins of photosystem II reaction centers (PSII) compared to a plant not comprising said at least one second nucleic acid molecule, and exposing said seeds or plants to said herbicide.

21. The method of claim 20, wherein said seeds or plants are exposed to said glyphosate and said herbicide sequentially or simultaneously.

22. The method of claim 20, wherein at least one of said seeds comprising said nucleic acid molecule and said at least one second nucleic acid molecule further comprises at least one third nucleic acid molecule encoding a polypeptide conferring increased resistance to a herbicide selected from the group consisting of α-ketoglutarate-dependent dioxygenase (AAD-12), hydroxyphenylpyruvate dioxygenase (HPPD), acetolactase synthase (ALS) enzyme, protoporphyrinogen oxidase (PPO), dicamba, glufosinate, phosphinothricin, bialaphos and which binds to core proteins of photosystem II reaction centers (PSII) and exposing said seeds or plants to said herbicide.

* * * * *